United States Patent
Wang et al.

(10) Patent No.: US 12,151,002 B2
(45) Date of Patent: Nov. 26, 2024

(54) NANOPARTICLE-ENABLED X-RAY MAGNETIC RESONANCE IMAGING (NXMRI)

(71) Applicant: RENSSELAER POLYTECHNIC INSTITUTE, Troy, NY (US)

(72) Inventors: Ge Wang, Loudonville, NY (US); Matthew Webber Getzin, Troy, NY (US); Lars Arne Gjesteby, Cohasset, MA (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 301 days.

(21) Appl. No.: 15/305,510

(22) PCT Filed: Apr. 21, 2015

(86) PCT No.: PCT/US2015/026919
§ 371 (c)(1),
(2) Date: Oct. 20, 2016

(87) PCT Pub. No.: WO2015/164405
PCT Pub. Date: Oct. 29, 2015

(65) Prior Publication Data
US 2017/0043041 A1    Feb. 16, 2017

Related U.S. Application Data

(60) Provisional application No. 61/981,878, filed on Apr. 21, 2014.

(51) Int. Cl.
*G01R 33/48*    (2006.01)
*A61B 5/00*    (2006.01)
(Continued)

(52) U.S. Cl.
CPC ........ *A61K 49/1824* (2013.01); *A61B 5/0035* (2013.01); *A61B 5/0042* (2013.01);
(Continued)

(58) Field of Classification Search
CPC ................ A61K 49/1824; A61K 49/08; A61K 49/04–0495; A61B 5/0035;
(Continued)

(56) References Cited

U.S. PATENT DOCUMENTS 6,818,202 B2 *  11/2004  Pines ................. A61K 49/1815
                                                                424/9.3
8,128,908 B2 *  3/2012  Santra ................ A61K 49/0002
                                                                424/9.3
(Continued)

FOREIGN PATENT DOCUMENTS

WO    WO-2014047518 A1 *  3/2014  ........... A61B 5/0035

OTHER PUBLICATIONS

Chen, Hongyu et al., "Monitoring pH-Triggered Drug Release from Radioluminescent Nanocapsules with X-ray Excited Optical Luminescence". ACS Nano, vol. 7, pp. 1178-1187 (Year: 2013).*
(Continued)

*Primary Examiner* — Keith M Raymond
*Assistant Examiner* — Milton Truong
(74) *Attorney, Agent, or Firm* — Barclay Damon LLC; Anthony P. Gangemi

(57) ABSTRACT

Imaging systems and methods are provided. Systems and methods of the subject invention can include the use of nanoparticles (for example, nanophosphors) within a sample to be imaged. Excitation with radiation, such as X-ray radiation, can be performed on the nanoparticles to give rise to a change in one or more resonance parameters of the nanoparticles, and this change can be measured using magnetic resonance imaging to provide localization information.

15 Claims, 35 Drawing Sheets

(51) Int. Cl.
| | |
|---|---|
| A61B 5/055 | (2006.01) |
| A61B 6/03 | (2006.01) |
| A61K 49/04 | (2006.01) |
| A61K 49/08 | (2006.01) |
| A61K 49/18 | (2006.01) |
| G01R 33/56 | (2006.01) |

(52) U.S. Cl.
CPC .............. *A61B 5/055* (2013.01); *A61B 6/032* (2013.01); *A61K 49/04* (2013.01); *A61K 49/08* (2013.01); *G01R 33/4812* (2013.01); *G01R 33/5601* (2013.01)

(58) Field of Classification Search
CPC ....... A61B 5/0042; A61B 5/055; A61B 6/032; G01R 33/4812; G01R 33/5601; G01R 33/4808
See application file for complete search history.

(56) References Cited

U.S. PATENT DOCUMENTS

| | | | | |
|---|---|---|---|---|
| 2006/0173362 | A1* | 8/2006 | Toms | A61B 5/411 600/478 |
| 2007/0104650 | A1 | 5/2007 | Cunningham et al. | |
| 2007/0269382 | A1* | 11/2007 | Santra | A61K 49/0002 424/9.323 |
| 2008/0255403 | A1 | 10/2008 | Voegele et al. | |
| 2010/0259259 | A1 | 10/2010 | Zahn et al. | |
| 2010/0303733 | A1* | 12/2010 | Hyde | A61K 49/1818 424/9.341 |
| 2011/0148414 | A1 | 6/2011 | Teughels et al. | |
| 2012/0265050 | A1* | 10/2012 | Wang | A61B 5/055 600/411 |
| 2014/0051974 | A1* | 2/2014 | Rapoport | A61B 5/0035 600/411 |
| 2014/0227186 | A1* | 8/2014 | Rademacher | A61K 39/3955 424/9.2 |
| 2014/0371575 | A1* | 12/2014 | Maldiney | A61K 49/0093 600/414 |

OTHER PUBLICATIONS

Lee, Nohyun et al. "Multifunctional Fe3O4/TaOx Core/Shell Nanoparticles for Simultaneous Magnetic Resonance Imaging and X-ray Computed Tomography". J. Am. Chem. Soc., vol. 134, pp. 10309-10312 (Year: 2012).*

Chen, H et al. "Magnetic and optical properties of multifunctional core-shell radioluminescence nanoparticles". J. Mater. Chem., 2012, 22, 12802 (Year: 2012).*

T. Maldiney et al. "Controlling Electron Trap Depth To Enhance Optical Properties of Persistent Luminescence Nanoparticles for In Vivo Imaging". J. Am. Chem. Soc. 2011, 133, 30, 11810-11815 (Year: 2011).*

N Basavaraju et al 2013. "Red persistent luminescence in MgGa2O4:Cr3+; a new phosphor for in vivo imaging". J. Phys. D: Appl. Phys. 46 375401 (Year: 2013).*

Chen, H. et al. "Advances in functional X-ray imaging techniques and contrast agents". Phys. Chem. Chem. Phys., 2012, 14, 13469-13486 (Year: 2012).*

Carpenter et al., "Radioluminescent nanophosphors enable multiplexed small-animal imaging," Optics Express, May 12, 2012, pp. 11598-11604, vol. 20, No. 11.

Qin et al., "Noninvasive detection of macrophages in atherosclerotic lesions by computed tomography enhanced with PEGylated gold nanoparticles," International Journal of Nanomedicine, Dec. 2, 2014, pp. 5575-5590, vol. 9, Dove Medical Press Limited.

Naha et al., "Dextran coated bismuth-iron oxide nanohybrid contrast agents for computed tomography and magnetic resonance imaging," Journal of Materials Chemistry B Materials for Biology and Medicine, Dec. 14, 2014, pp. 8239-8248, vol. 2, No. 46.

Cong et al., "Stored luminescence computed tomography," Applied Optics, Sep. 2013, pp. 5672-5676, vol. 53.

Cong et al., "X-ray micro-modulated luminescence tomography (XMLT)," Optics Express, Mar. 10, 2014, pp. 5572-5580, vol. 22, No. 5.

Chuang et al., "Photostimulable near-infrared persistent luminescent nanoprobes for ultrasensitive and longitudinal deep-tissue bio-imaging," Theranostics, Aug. 24, 2014, pp. 1112-1122, vol. 4, No. 11, Ivyspring International Publisher.

Elster, "Advanced relaxation theory," Questions and Answers in MRI, 2014, http://www.mri- q.com/solomon-bloembergen.html.

Liu et al., "Photostimulated near-infrared persistent luminescence as a new optical read-out from Cr3+-doped LiGa5O8," Science Reports, Mar. 27, 2013, pp. 1-9, vol. 3.

Maldiney et al., "Controlling electron trap depth to enhance optical properties of persistent luminescence nanoparticles for in vivo imaging," Journal of the American Chemical Society, Jun. 24, 2011, pp. 11810-11815, vol. 133, No. 30.

Laurent et al., "Lanthanide complexes for magnetic resonance and optical molecular imaging," The Quarterly Journal of Nuclear Medicine and Molecular Imaging, Dec. 2009, pp. 586-603, vol. 53, No. 6.

Chen et al., "Monitoring pH-triggered drug release from radioluminescent nanocapsules with x-ray excited optical uminescence," ACS Nano, Jan. 2013, pp. 1178-1187, vol. 7, No. 2.

Getzin et al., "Carotid plaque characterization using CT and MRI for synergistic analysis," SPIE Optical Engineering+ Applications, 2014, p. 92121B.

Getzin et al., "A pilot study on coupling CT and MRI through use of semiconductor nanoparticles," arXiv Preprints, 2014.

International Search Report and Written Opinion, International Application No. PCT/US2015/026919, mail date Jul. 29, 2015, PCT/ISA/210, PCT/ISA/220, PCT/ISA/237.

* cited by examiner

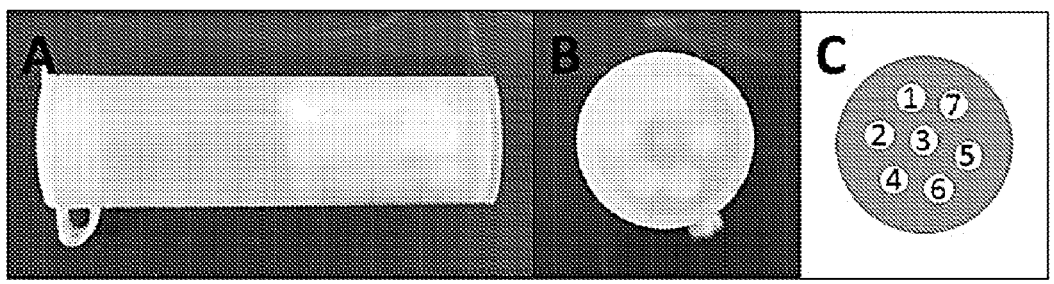
FIG. 30A　　　　　FIG. 30B　　　　　FIG. 30C
 
FIG. 31A　　　　　FIG. 31B

NANOPARTICLE-ENABLED X-RAY MAGNETIC RESONANCE IMAGING (NXMRI)

CROSS-REFERENCE TO RELATED APPLICATION

This application is a national stage application of International Patent Application No. PCT/US2015/026919, filed Apr. 21 2015, which claims the benefit of U.S. Provisional Application Ser. No. 61/981,878, filed Apr. 21, 2014, both of which are incorporated herein by reference in their entireties.

BACKGROUND OF INVENTION

The study of biological systems is a complex pursuit that requires sufficient models and tools to measure responses to controlled changes in the system. Such models include simulations, two-dimensional (2D) and three-dimensional (3D) in vitro constructs, and in vivo animal and human models. These can be studied at varying levels of scale that span from molecular to whole-organism behavior. To measure changes on the smaller end of the scale, imaging tools including microscopes and in vivo bio-imaging modalities, as well as nucleic acid and protein quantification tools, can be utilized. These tools can be especially useful in regenerative medicine studies where slight changes on the cellular and molecular level can induce radical changes in the overall model. Therefore, correct use of the imaging tools for accurate assessment of constructs is of utmost importance.

Optical imaging methods such as microscopy have dominated the realm of 2D cellular and molecular imaging research. Microscopy has allowed for much insight into the mechanisms of cellular and molecular function. However, these insights have been limited to 2D and thin 3D models because of the diffusive properties of optical light. In order to study more complex systems with 3D interactions, imaging modalities must evolve to allow for deeper imaging. Computed tomography (CT) and magnetic resonance imaging (MRI) are two well-established modalities that are capable of imaging deep tissues that elude optical methods. CT uses an X-ray source to irradiate a region of interest. X-ray detectors are set up on the other side of the sample and can measure both the power and the spectra of the X-rays that transverse the sample. Contrast occurs due to the varying attenuation that different tissue types have on the X-rays. MRI, on the other hand, uses large homogeneous magnetic fields and strategic radio frequency (RF) pulse sequences to determine the concentration and surrounding environment for nuclei of interest. The value of a single voxel is the vector sum of the magnetic resonance of all of the nuclei of interest in a given volume.

Chemical shift-based MRI methods are often used to separate water and fat signals from the acquired images. The mechanism on which this method is based is the variation in the local magnetic fields for the nuclei of interest. In the case of fat-suppression MRI, the H1 proton of lipid rich tissues has a different magnetic resonance than that of the H1 proton in water. This difference (chemical shift) is measured in parts per million and depends on the chemical environment of the given isotope.

Conventional forms of molecular imaging, such as positron emission tomography (PET), single-photon emission computed tomography (SPECT), and fluorescence resonance energy transfer (FRET), offer extremely high specificity in imaging and increase understanding of some molecular functionality. Despite these strengths, however, they are limited in their spatial and temporal resolution. Fluorescence-based imaging, especially, has limitations in terms of imaging depth.

BRIEF SUMMARY

The subject invention provides novel and advantageous imaging systems and imaging methods, capable of overcoming the limitations of related art imaging methods and systems. Systems and methods of the subject invention can include the use of nanoparticles (for example, nanophosphors) within a sample to be imaged. Excitation with radiation, such as ultraviolet (UV) or X-ray radiation, can be performed on the nanoparticles to affect one or more resonance parameters of the nanoparticles. That is, after excitation, the change in energy state of the nanoparticles can affect the local magnetic fields surrounding the nanoparticles, and, when in a magnetic resonance imaging (MRI) machine, this change can be measured as a change in one or more resonance constants (for example, T1, T2, and/or T2*) of the nanoparticles. This can provide localization information in imaging (including but not limited to in vivo imaging such as brain, cardiac, and cancer imaging) as a long-term, dynamic contrast agent.

In an embodiment, an imaging method can include: providing nanoparticles to a sample to be imaged; using a radiation source to excite the nanoparticles; and imaging the sample using MRI to obtain localization information of the nanoparticles by measuring a change in a resonance parameter of the nanoparticles as a result of the excitation by the radiation source.

In another embodiment, an imaging system can include: a radiation source configured to supply radiation to nanoparticles provided within a sample to be imaged; an MRI machine configured to obtain a magnetic resonance image of the sample before and after excitation by the radiation source; and a processor configured to determine localization information of the nanoparticles provided within the sample by measuring a change in a resonance parameter of the nanoparticles as a result of the excitation by the radiation source.

BRIEF DESCRIPTION OF THE DRAWINGS

FIG. 30A shows a side view of capillary tubes having nanoparticles and tubes having water.

FIG. 30B shows a side view of capillary tubes having nanoparticles and tubes having water.

FIG. 30C shows a schematic view of capillary tubes having nanoparticles and tubes having water.

FIG. 31A shows a microscopy image of UV pre-excited nanophosphor powder with laser stimulation off.

FIG. 31B shows a microscopy image of the UV pre-excited nanophosphor powder of FIG. 40A, with laser stimulation on.

DETAILED DESCRIPTION

Figure 1:
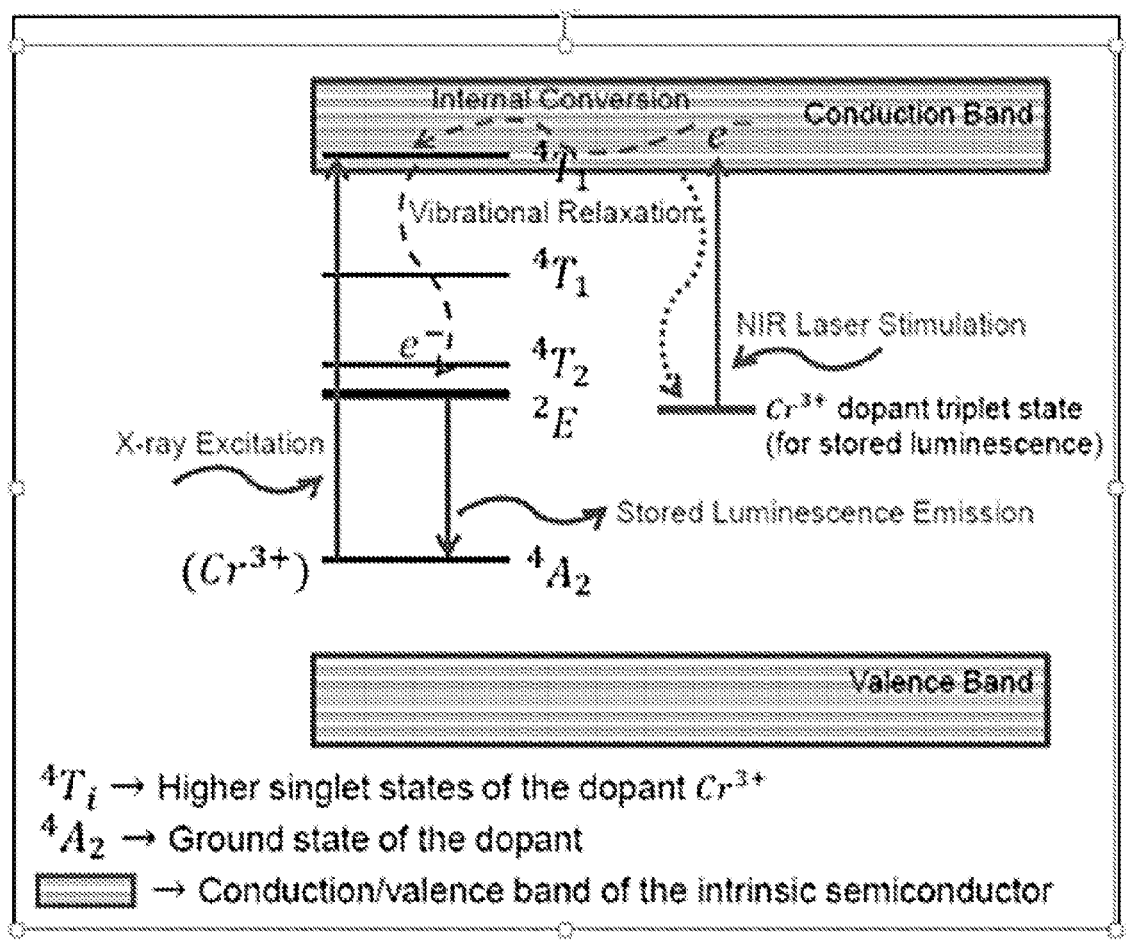
FIG. 1 shows an energy diagram of doped semiconductors for stored nanophosphor luminescence.

The subject invention provides novel and advantageous imaging systems and imaging methods, capable of overcoming the limitations of related art imaging methods and systems. Systems and methods of the subject invention can include the use of nanoparticles (for example, nanophosphors) within a sample to be imaged. Excitation with radiation, such as ultraviolet (UV) or X-ray radiation, can be performed on the nanoparticles to affect one or more resonance parameters of the nanoparticles. That is, after excitation, the change in energy state of the nanoparticles can affect the local magnetic fields surrounding the nanoparticles, and, when in a magnetic resonance imaging (MRI) machine, this change can be measured as a change in one or more resonance constants (for example, T1, T2, and/or T2*) of the nanoparticles. This can provide localization information in imaging (including but not limited to in vivo imaging such as brain, cardiac, and cancer imaging) as a long-term, dynamic contrast agent. Nanoparticles can reach and remain in areas of a body (e.g., a human body) that conventional contrast fluids may not be able to (for example, through the blood brain barrier).

The subject invention provides multi-physics coupling techniques. Through the combination of certain techniques, including radiation (e.g., X-ray or UV) excitable nanoparticles, chemical shift imaging, and/or interior tomography, the subject invention provides new approaches for molecular imaging without the limitations of related art methods. In certain embodiments, principles of computed tomography (CT) can be combined with MRI; for example, a combined CT-MRI scanner can be used for simultaneous or nearly simultaneous excitation and imaging.

In many embodiments, resonance parameters (e.g., T1, T2, and/or T2*) of nanoparticles can be modulated by excitation of the nanoparticles by irradiating (e.g., UV or X-ray irradiation) the nanoparticles. For example, the T2 relaxation time of nanoparticles can be modulated by X-ray excitation and measured by MRI. Irradiation-excited (e.g., X-ray-excited) nanophosphors simultaneously enable high-resolution imaging, biological targeting, and enhanced MRI soft tissue contrast in vivo or in situ. The nanoparticles can be nanophosphors, though embodiments are not necessarily limited thereto. The nanophosphors can be semiconducting crystals, which can be doped (e.g., with lanthanide ions), though embodiments are not limited thereto. Nanophosphors that can be used can include, for example, $LiGa_5O_8$ (which can be doped with, e.g., $Cr^{3+}$), $MgGa_2O_4$ (which can be doped with, e.g., $Cr^{3+}$), $CaMgSi_2O_6$ (which can be doped with $Eu^{2+}$, $Mn^{2+}$, or $Pr^{3+}$), or $Gd_2O_2S$ (which can be doped with, e.g., $Tb^{3+}$), though embodiments are not limited thereto.

Irradiation-excited (e.g., X-ray-excited) electrons in nanophosphors can change the local magnetic field in a measurable way, which can specifically lead to measurable changes in resonance parameters, such as MRI relaxation parameters, before and after excitation. This technique can be referred to as nanoparticle-enabled excitation MRI or nanoparticle-enabled X-ray MRI (NXMRI) can synergistically blend merits of optical imaging, CT, and MRI. Imaging hardware capable of simultaneous CT-MRI imaging can be used, or separate devices for excitation and MRI can be used.

Although CT and MRI have seemingly contradicting acquisition mechanisms (CT-spinning metal detectors, MRI-large magnetic field), the datasets of CT and MRI can be quite complimentary. Also, in a simultaneous acquisition system, the imaging physics of CT and MRI can be used to alter the imaged system and, therefore, the acquired signal for new information not previously known. Systems and methods of the subject invention can apply this concept of multi-physics coupling as a means for targeted, high resolution (spatial, contrast, and temporal) imaging. Nanoparticles can be used as a coupling mechanism between different imaging modalities (e.g., CT and MRI). In certain embodiments, the nanoparticles can be made of doped semiconducting materials that store energy in the form of high energy electrons after irradiation by high energy electromagnetic radiation. The irradiation can be, e.g., UV or X-ray irradiation. After excitation, the change in energy state in the nanoparticles can affect the local magnetic fields surrounding the nanoparticles. When placed in an MRI machine, this can be measured as a change in the resonance constants (e.g., T1, T2, and/or T2*). This can allow for faster scanning as focused CT can provide a mechanism of knowing spatial information of an object being imaged without the need for all the complex and time-consuming magnetic gradients that are used in related art MRI technologies. CT can also offer superior combinations of spatial resolution and imaging speed compared to MRI, and by combining the modalities and using highly specific targeted nanoparticles, spatial, contrast, and temporal resolution can be achieved on levels not previously achieved in in vivo imaging.

Systems and methods of the subject invention can advantageously allow for simultaneous acquisition (e.g., using CT and MRI), giving high correlation between the images obtained by both systems to be linked with use of nanoparticles. Because the information seen in CT and MRI are different yet can work together synergistically, simultaneous acquisition can remove the limitations of combining their information, which includes delays in acquisition between modalities, motion artifacts, and poor slice/ROI (region of interest) registration. By coupling these systems, the acquisition physics of each modality can advantageously be used to induce the information measured by the other method. This multi-physics coupling can be seen as an effect of the large magnetic fields on the X-ray scattering within the system or as changes in the local resonance constants (T1, T2, T2*) due to X-ray radiation (e.g., in biological tissues). The subject invention can allow for spatial information to be obtained much faster than related art technologies; this can be done by largely bypassing the need for gradient coils and frequency and phase encoding. Focused irradiation (e.g., focused X-ray beams) can be used for excitation, giving a high level of control over where the irradiation is focused and, therefore, where the local magnetic field changes occur. The irradiation energy (e.g., X-ray energy) can be highest in the focal spot of the beam, but energy can be deposited and distributed into the tissue in "gradient-like" fashion, giving rise to spatially varying resonance changes without the need for the gradient coils. In certain embodiments, an exogenous material can be introduced to the system to change the measurable signals in a way that can be predicted.

In an embodiment, a CT-MRI scanner can be used for nanoparticle-based CT-MRI coupling for imaging, radiation therapy, and research, among other applications. A system can include magnets, such as permanent magnets to form a regionally uniform magnetic field while leaving room for a stationary CT gantry. For example, a double donut-shaped pair of permanent magnets can form a regionally uniform magnetic field (e.g., about 0.5 Tesla) and leave room for a stationary 9-source interior CT gantry at 3 tube voltages (triple-energy CT). Spatiotemporal correlation of complicated features and multi-physics coupling based parameters can be extracted. In another embodiment, nanoparticles, X-ray imaging, and MRI can be integrated. Because X-rays modulate distributions of electrons inside nanoparticles and change MRI parameters (e.g., T2), improved imaging can be achieved as discussed herein. In another embodiment, single or multiple X-ray beams can be combined with a simplified magnetic setup for NXMRI. Embodiments of the subject invention provide synergy from synchrony and coupling that can advantageously benefit may fields, including biomedicine.

Nanoparticles can be used in a variety of biomedical applications, including drug delivery and medical imaging. The chemistry of these particles can be controlled for highly specific targeting using antibodies. Functionalization in this way can allow for the nanoparticles to act as probes for cellular and molecular imaging. Through functional-group customization, the nanoparticles can be adjusted based on the application, region, molecule, tissue, or cell type of interest. Also, in the same way that the proton resonance of fat and water vary, so too should the resonance of given nuclei of a nanoparticle at low- and high-energy states.

In addition to their targeting ability, nanoparticles can be designed to perform a number of functions including drug delivery to imaging enhancement. One class of image enhancement nanoparticles that can be particularly useful is the nanophosphor group of nanoparticles. These particles can be made of inherent semiconducting molecules and subsequently doped with rare earth ions. This type of formulation gives the manufacturer the ability to use some form of electromagnetic (EM) radiation (e.g., visible light, ultraviolet (UV), X-ray) to excite the nanoparticles and induce a "trapping" of high energy electrons between the valence and conducting bands of the electron shell. Over time or after subsequent stimulation of the excited nanophosphor (NP) with another form of EM radiation, the energy can be released as light (luminescence), such as visible or near-infrared (NIR) light. The energy of these electrons and the persistence (length of time) of the trap can be customized by changing the nanoparticle formulation and/or doping ion. Types of energy storage that can be achieved by nanophosphors include immediate luminescence, persistent luminescence, and stored luminescence with stimulated release.

Figure 2A:
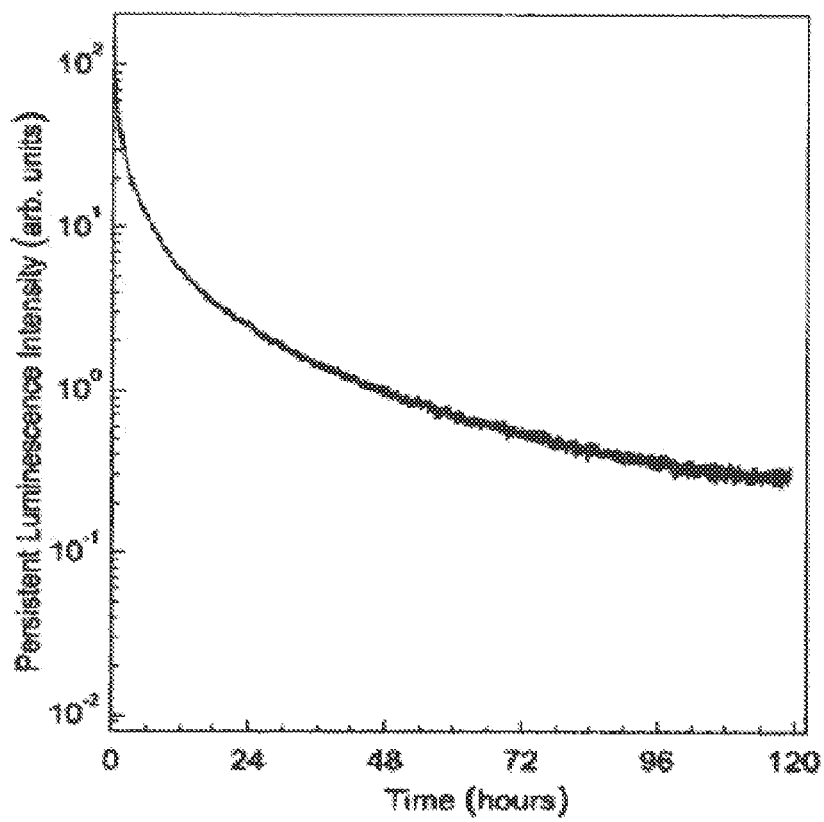
FIG. 2A shows a plot of persistent luminescence intensity versus time.
Figure 2B:
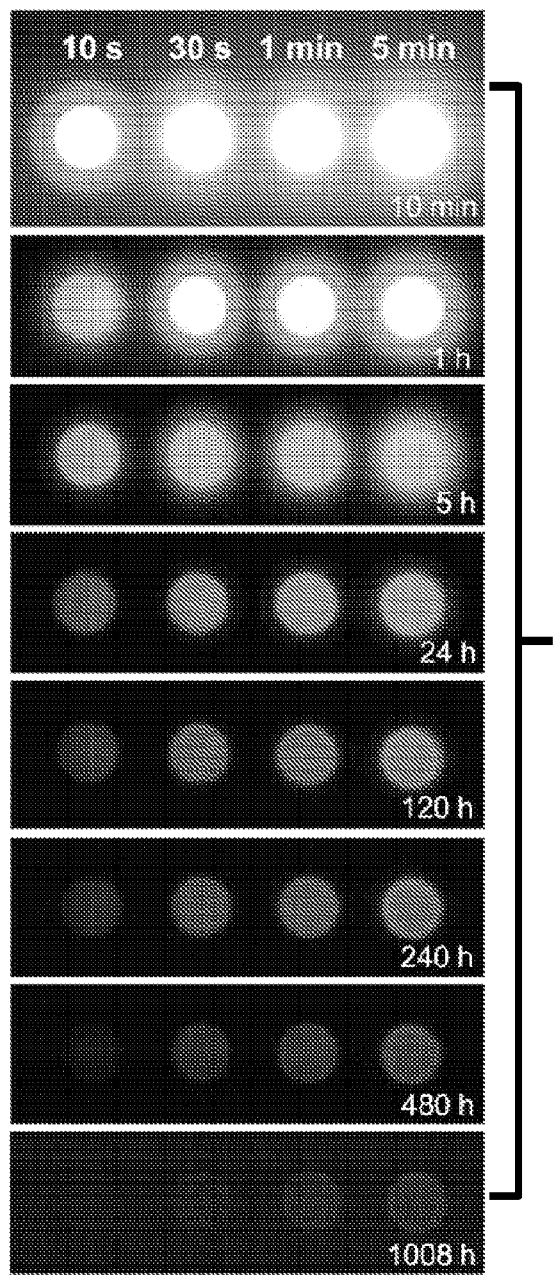
FIG. 2B shows near-infrared (NIR) images of four phosphor discs taken at different persistent luminescence times.

Nanophosphors that exhibit immediate release of the transferred energy in the form of luminescence can be said to have immediate luminescence. Persistent luminescence nanoparticles refer to a type of nanoparticle that can absorb EM radiation at wavelengths specific to its chemical and physical properties, and remain in that higher energy state for prolonged periods of time. Compositions of such nanoparticles can vary slightly, though some commonly used chemistries include $MgGa_2O_4:Cr^{3+}$ and $CaMgSi_2O_6:Eu^{2+}$, $Mn^{2+},Pr^{3+}$. The commonality of these energy-storing nanoparticles is the presence of the rare earth ions. These can act as electron traps whose optical properties can be adjusted through the addition of more doping ions, effectively "deepening" the trap. FIG. 1, which shows an energy diagram of doped semiconductors for stored nanophosphor luminescence, illustrates this process. The persistence of the luminescence that these excitable nanophosphors are capable of emitting is evidence of energy storage of such nanoparticles. Irradiated nanophosphors can exhibit persistent luminescence for up to 1,000 hours after excitation (Liu et al., 2013); FIGS. 2A and 2B summarize the results of Liu et al. (2013). FIG. 2A shows an NIR persistent luminescence decay curve monitored at 716 nm after irradiation by 300-nm light for 20 minutes. The discs persistent luminescent $LiGa_5O_8:Cr^{3+}$ phosphor discs. FIG. 2B NIR images of four persistent luminescent $LiGa_5O_8:Cr^{3+}$ phosphor discs taken at different persistent luminescence times (10 minutes to 1,008 hours) after irradiation by a 254-nm lamp for 10 seconds to 5 minutes.

Figure 3:
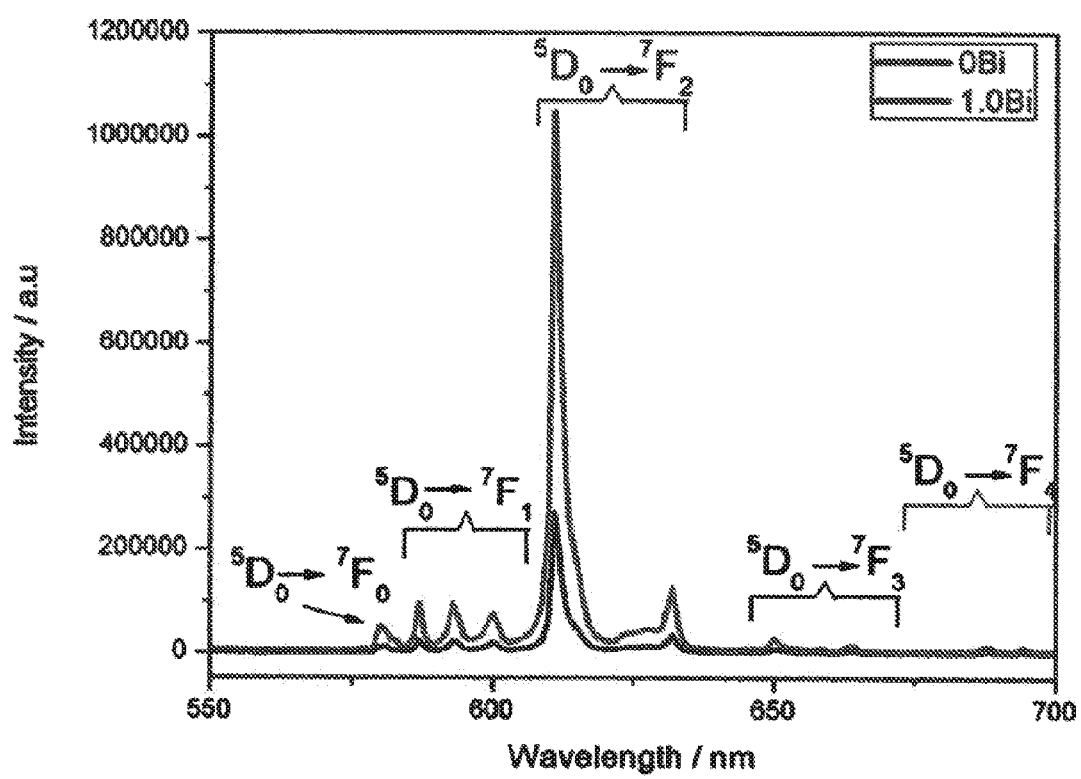
FIG. 3 shows optical emission spectra for nanoparticles.

Energy transfer mechanisms for these nanoparticles can be highly dependent on the particle composition, but they can be excited with both UV and X-ray radiation. Various silicon nanostructures can absorb energy such that their excited state has an increase of about 2-7 eV over resting state particles. This change in energy is directly related to the fluorescent emissions that can be seen immediately or elicited at later time points from subsequent excitation with NIR radiation. The optical emission spectra of lutetium oxide nanoparticles after UV excitation are displayed in FIG. 3. FIG. 3 shows the optical emission spectra for $Lu_2O_3$: 2.5 at % $Eu^{3+}$, 1.0 at % $Bi^{3+}$ after excitation from 330 nm UV light. This fluorescence emission can be attributed to an increase in energy that redistributes the nanoparticle's electrons within its energy shells. This change in energy can be measurable in changes in the nanoparticle's resonance characteristics.

Beam geometry is a consideration when exciting nanophosphors with X-rays in a target region, such as a target region of a body (e.g., a brain). Fan beam and pencil beam geometries offer precise targeting of biology, but they are best suited for 2D imaging purposes. For the targeting of nanophosphors in the body, precise 3D beam geometry is preferable while minimizing radiation. The method of interior tomography can help deal with such a challenge. Interior tomography enables exact reconstruction of an internal region of interest (ROI) while requiring only the projection data through that ROI. The geometry used in interior CT is spiral cone-beam. This facilitates narrower beams, eliminates unnecessary radiation, and reduces scan times as compared to global tomographic reconstruction. Because specificity is of utmost importance when passing X-rays through a body (e.g., a human body), the principles of interior CT offer a benchmark in the excitation of nanophosphors in the brain.

Micro-modulated luminescence tomography (MLT) and stored luminescence computed tomography (SLCT) are multi-modality tools that utilize the penetration depth of CT and the specificity of optical molecular probes. Both of these mechanisms require the sample to be exposed to X-ray excitable nanoparticles. These nanoparticles can be specifically designed to attach to a certain cell type or protein. Once the nanoparticles have been given time to distribute and attach to their target molecules, an X-ray source can be focused on the ROI and used to excite the nanoparticles to a high-energy state. The nanoparticles can remain at this high energy state for hours at a time or, through NIR excitation, the energy can be released as optical energy in the NIR range. However, because the measured signal is still in the optical range, penetration depth remains an issue.

MLT and SLCT technologies can allow for enhancing resolution of acquired data in comparison to conventional molecular imaging techniques. These techniques can use doped semiconductors that can be tagged to specifically bind to the area of interest. Through strategic collimation and focusing of the X-ray source, nanoparticles in specified areas of interest can be excited with a relatively low X-ray dose. This allows for a whole new level of imaging specificity. MLT and SLCT can use optical pairing in order to acquire the luminescent signal from the excited nanoparticles. These techniques, despite their increased penetration depth compared to techniques such as FRET, may still be limited in this area. Therefore, the systems and methods of the subject invention can provide advantages over existing imaging modalities.

Chemical shift imaging methods can be used to separate water and fat signals from acquired MRI data. Because the molecular structure of the hydrogen protons of fat and of water are different, a shift in the resonant frequency of these protons results. This shift can cause a misrepresentation of the location of fatty signals relative to the water signals. In addition to this difference in resonant (Larmor) frequency, spin relaxation times (T1, T2, and T2*) can also be affected by the surrounding electric and magnetic environment (i.e., protons in fat versus protons in water). Radio frequency (RF) pulse sequences can be adjusted to isolate water and fat signals. These same principles can be applied to other endogenous nuclei of interest, including phosphorus-31 and carbon-13. Chemical shifts in phosphorus-31 nuclei can enable detection of alterations in cardiac phosphate metabolism. Similarly, exogenous molecules, such as nanoparticles, can be used as the target nuclei in magnetic resonance chemical shift imaging.

In many embodiments of the subject invention, nanoparticle-mediated X-ray magnetic resonance imaging (NXMRI) can use X-ray excited nanophosphors in chemical shift-based MRI. Nanophosphors can enable imaging (e.g., biological imaging such as brain imaging) at depths unattainable by existing techniques. Energy storing nanoparticles can be used with optical imaging to image nanophosphor distribution in depths of greater than 5 mm (e.g., such depths in a brain). While a depth of 5 mm is much deeper than current microscopy techniques including electron microscopy, it still only accounts for the cortex of the brain. Using MRI, deeper regions containing nanophosphors can be imaged and analyzed according to embodiments of the subject invention, based on changes in their spin relaxation properties due change in energy state induced by X-ray irradiation. Relaxation time T2 (or $T_2$), also referred to as transverse or spin-spin relaxation time, can show the largest difference. The effects that X-ray excitation has on the T2 property of nanophosphors during MRI show that NXMRI can have a wide range of applications.

Figure 4:
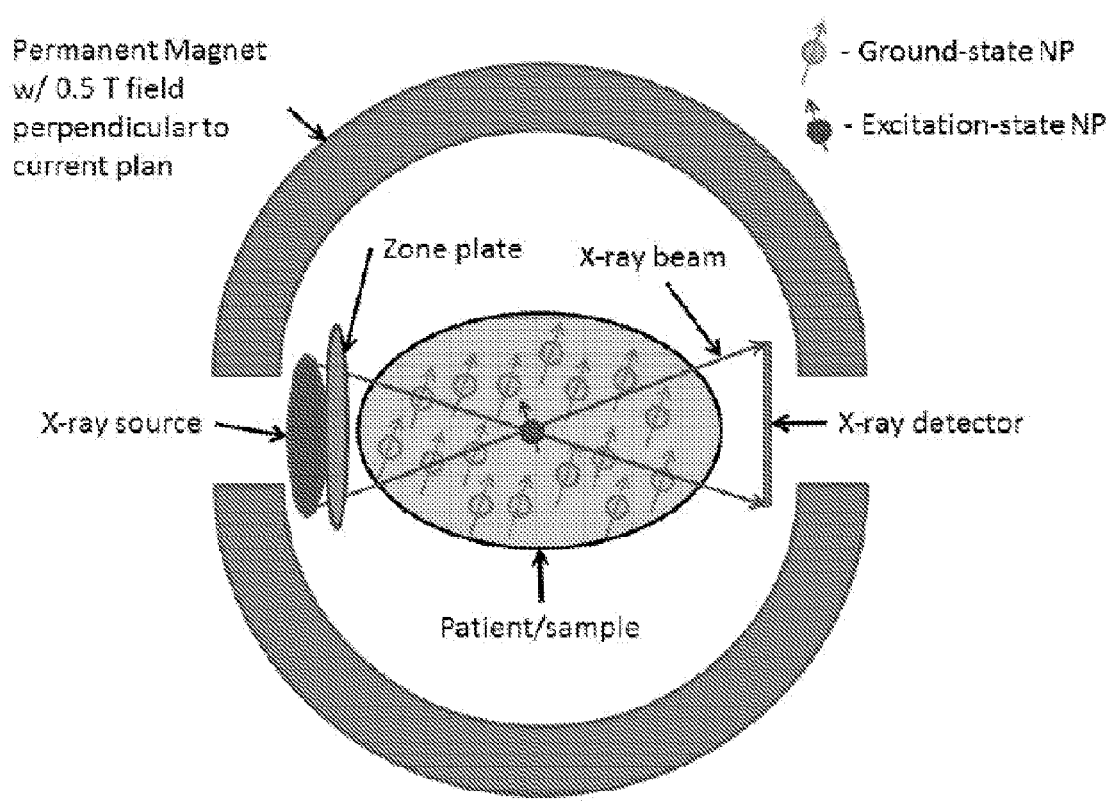
FIG. 4 shows a schematic view of nanoparticle-enabled X-ray magnetic resonance imaging.

FIG. 4 shows a schematic view illustrating the mechanism of NXMRI according to certain embodiments of the subject invention. Referring to FIG. 4, nanoparticles can be excited by X-rays, causing stored and/or persistent luminescence of the nanophosphors. MRI can be used to measure the change in resonance characteristics (e.g., relaxation time such as T2 relaxation time) of the nanophosphors before and after excitation. Though FIG. 4 shows that a permanent magnet with a 0.5 Tesla (T) field is used, this is for exemplary purposes only; embodiments of the subject invention are not limited thereto.

The ability to distinguish signals from low- or high-energy nanoparticles can depend on a number of factors. One factor is the effective range between the respective Larmor frequencies of the low- and high-energy nanoparticles. Resonance in porous silicon-based nanoparticles can increase in high-energy nanoparticles on the order of hundreds of THz (same frequency as emitted radiation). The larger the difference between the spectra of these two states, the more accurate separation of signal can be achieved. The ability to use frequency encoding for spatial mapping is another important consideration. Because the Larmor frequencies may differ slightly between low- and high-energy state nanoparticles, the spatial registration of the resulting signals can vary between acquisitions. This can largely be compensated for via various image analysis algorithms. Additionally, interior tomography principles can be applied to MRI in order to improve spatial and temporal resolution of chemical shift imaging. This can be achieved by using a time-varying gradient magnetic field in an area that includes only the ROI, while maintaining a homogeneous main magnetic field elsewhere.

Embodiments of the subject invention, including NXMRI, have many high impact applications, including improving imaging techniques that can be used to map and collect functional data in vivo, including data of the brain (e.g., a human brain). Deep signal extraction is a challenge in brain imaging, and embodiments of the subject invention provide solutions to this challenge. Because both X-rays and radio waves are easily transmittable through the skull and brain tissue, the excitation and measurement of nanoparticles (e.g., nanophosphors) can be done in areas that often cannot be studied with current technology. In addition to brain imaging, cancer detection and treatment monitoring can also benefit from embodiments of the subject invention. The nanoparticles (e.g., nanophosphors) can serve as a contrast agent to be introduced to regions of the body that are challenging to reach, such as the prostate. Chemical shift imaging can be effective in detecting prostate cancer tumors. Because about 20% of prostate cancers develop in the transition zone, which is the region of the prostate surrounding the proximal urethra, these tumors can be difficult to image using related art techniques, such as MRI, due to inconsistent ratios of choline plus creatine to citrate. Embodiments of the subject invention can therefore be used for improved monitoring for prostate cancer.

Embodiments of the subject invention can also be useful in cardiac imaging, where chemical shift imaging can be used to identify precursors to heart disease in patients with hereditary hemochromatosis (HHC). Chemical shift MRI with phosphorus-31P can enable the detection of alterations of cardiac high-energy phosphate metabolism in patients with HHC. Such patients have a high risk of developing heart disease, but have not exhibited any prior evidence, so embodiments of the subject invention can improve early diagnosis rates.

The systems, methods, and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals.

The subject invention includes, but is not limited to, the following exemplified embodiments.

Embodiment 1

An imaging method, comprising:
providing nanoparticles to a sample to be imaged;
using a radiation source to excite the nanoparticles; and
imaging the sample using magnetic resonance imaging (MRI) to obtain localization information of the nanoparticles by measuring a change in a resonance parameter of the nanoparticles as a result of the excitation by the radiation source.

Embodiment 2

The imaging method according to embodiment 1, wherein the nanoparticles are nanophosphors.

Embodiment 3

The imaging method according to embodiment 2, wherein the nanophosphors are semiconducting crystals doped with lanthanide ions.

Embodiment 4

The imaging method according to any of embodiments 1-3, wherein the resonance parameter of the nanoparticles is T2 relaxation time.

Embodiment 5

The imaging method according to any of embodiments 1-4, wherein the radiation source is an X-ray source such that the nanoparticles are excited with X-ray radiation.

Embodiment 6

The imaging method according to any of embodiments 1-5, wherein the sample to be imaged is a biological sample.

Embodiment 7

The imaging method according to any of embodiments 1-6, wherein the sample is living tissue such that the method is performed in vivo.

Embodiment 8

The imaging method according to embodiment 7, wherein the living tissue is living tissue of a human patient.

Embodiment 9

The imaging method according to any of embodiments 7-8, wherein the living tissue is a brain or part of a brain.

Embodiment 10

The imaging method according to any of embodiments 1, 2, or 4-9, wherein the nanoparticles include $LiGa_5O_8:Cr^{3+}$, $MgGa_2O_4:Cr^{3+}$, $Gd_2O_2S:Tb^{3+}$, $CaMgSi_2O_6:Eu^{2+}$, $CaMgSi_2O_6:Mn^{2+}$, $CaMgSi_2O_6:Pr^{3+}$, or a combination thereof.

Embodiment 11

The imaging method according to any of embodiments 1-3 or 5-10, wherein the resonance parameter is T1, T2, or T2*.

Embodiment 12

The imaging method according to any of embodiments 1-11, wherein imaging the sample using MRI to obtain localization information of the nanoparticles by measuring a change in a resonance parameter of the nanoparticles as a result of the excitation by the radiation source comprises measuring the resonance parameter of the nanoparticles before and after excitation by the radiation source.

Embodiment 13

The imaging method according to any of embodiments 1-4 or 6-12, wherein the radiation source is an ultraviolet (UV) source such that the nanoparticles are excited with UV radiation.

Embodiment 14

The imaging method according to any of embodiments 1-13, further comprising obtaining computed tomography (CT) data from the sample simultaneously while imaging the sample using MRI.

Embodiment 15

An imaging system, comprising:
a radiation source configured to supply radiation to nanoparticles provided within a sample to be imaged;
an MRI machine configured to obtain a magnetic resonance image of the sample before and after excitation by the radiation source; and
a processor configured to determine localization information of the nanoparticles provided within the sample by measuring a change in a resonance parameter of the nanoparticles as a result of the excitation by the radiation source.

Embodiment 16

The imaging system according to embodiment 15, wherein the nanoparticles are nanophosphors.

Embodiment 17

The imaging system according to embodiment 16, wherein the nanophosphors are semiconducting crystals doped with lanthanide ions.

Embodiment 18

The imaging system according to any of embodiments 15-17, wherein the resonance parameter of the nanoparticles is T2 relaxation time.

Embodiment 19

The imaging system according to any of embodiments 15-18, wherein the radiation source is an X-ray source configured to supply X-ray radiation to the nanoparticles.

Embodiment 20

The imaging system according to any of embodiments 15-19, wherein the sample to be imaged is a biological sample.

Embodiment 21

The imaging system according to any of embodiments 15-20, wherein the sample is living tissue such that the system is capable of performing in vivo imaging.

Embodiment 22

The imaging system according to embodiment 21, wherein the living tissue is living tissue of a human patient.

Embodiment 23

The imaging system according to any of embodiments 21-22, wherein the living tissue is a brain or part of a brain.

Embodiment 24

The imaging system according to any of embodiments 15, 16, or 18-23, wherein the nanoparticles include $LiGa_5O_8:Cr^{3+}$, $MgGa_2O_4:Cr^{3+}$, $Gd_2O_2S:Tb^{3+}$, $CaMgSi_2O_6:Eu^{2+}$, $CaMgSi_2O_6:Mn^{2+}$, $CaMgSi_2O_6:Pr^{3+}$, or a combination thereof.

Embodiment 25

The imaging system according to any of embodiments 15-17 or 19-24, wherein the resonance parameter is T1, T2, or T2*.

Embodiment 26

The imaging system according to any of embodiments 15-18 or 20-25, wherein the radiation source is a UV source configured to supply UV radiation to the nanoparticles.

Embodiment 27

The imaging system according to any of embodiments 15-26, further comprising a computed tomography mechanism integrated with the MRI machine to provide an integrated CT-MRI machine configured to simultaneously obtain CT data and MRI data from the sample.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 5:
FIG. 5 shows an image of phosphorescent powders.

Europium-doped aluminate oxide powders were scanned using MRI. Green Europium-doped aluminate oxide powder in an amount of 900 mg was mixed in 3 mL of deionized water. The powder was excited using UV for 30 minutes. Violet europium-doped aluminate oxide powder in an amount of 900 mg was also mixed in 3 mL of deionized water and excited using UV for 30 minutes. FIG. 5 shows an image of the bottles of the green and violet powders. MRI scans were run at time=0, 1 hour, 2 hours, and about 12 hours. Tripilot scanning was used. RAREVTR (8 repetition time (TR)) pulse sequencing was used to measure T1, and multi-slice multi-echo (MSME) (16 echo time (TE)) was used to measure T2 relaxation time.

Figure 6:
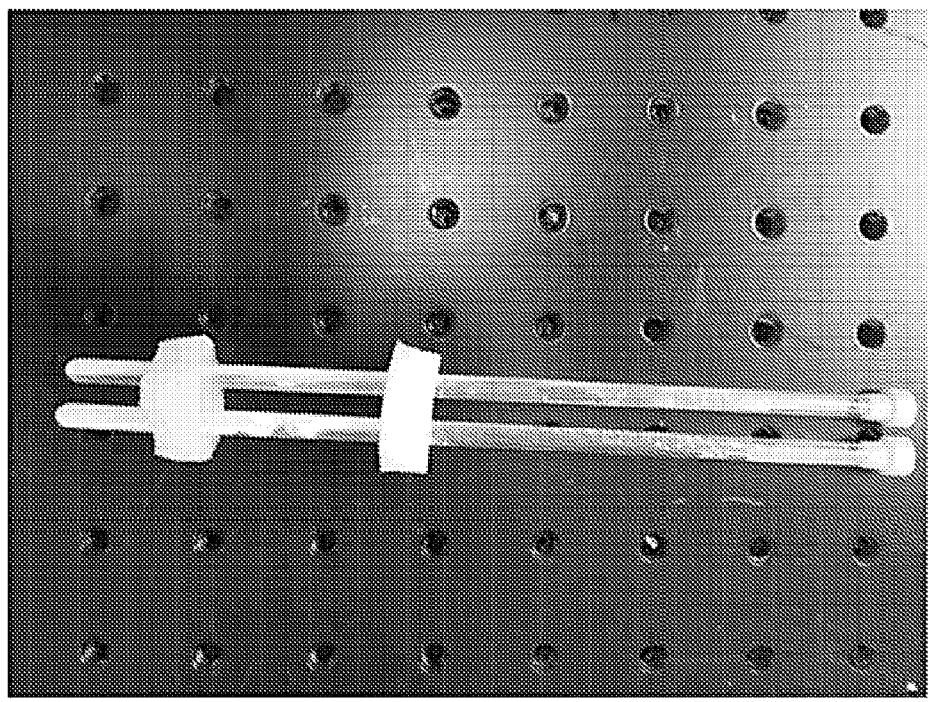
FIG. 6 shows an image of tubes having phosphorescent powders.

The powders quickly settled out of the solution, in less than 5 minutes. FIG. 6 shows an image of the powders in the water. The water seemed to "quench" the observable phosphorescence, and after some time (about 12-24 hours), the powders became more of a paste than a slurry. Interactions between the water and the powders seemed to be limited.

Figure 7:
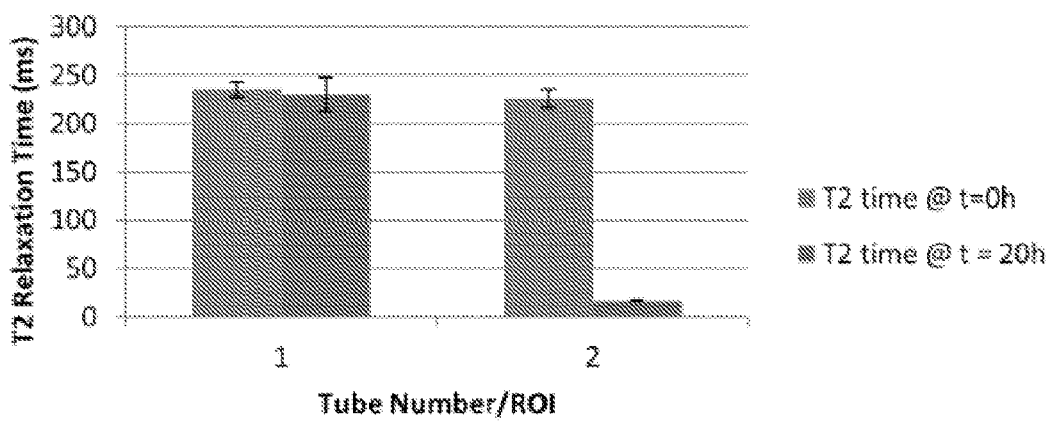
FIG. 7 shows a plot of $T_2$ relaxation time.
Figure 8:
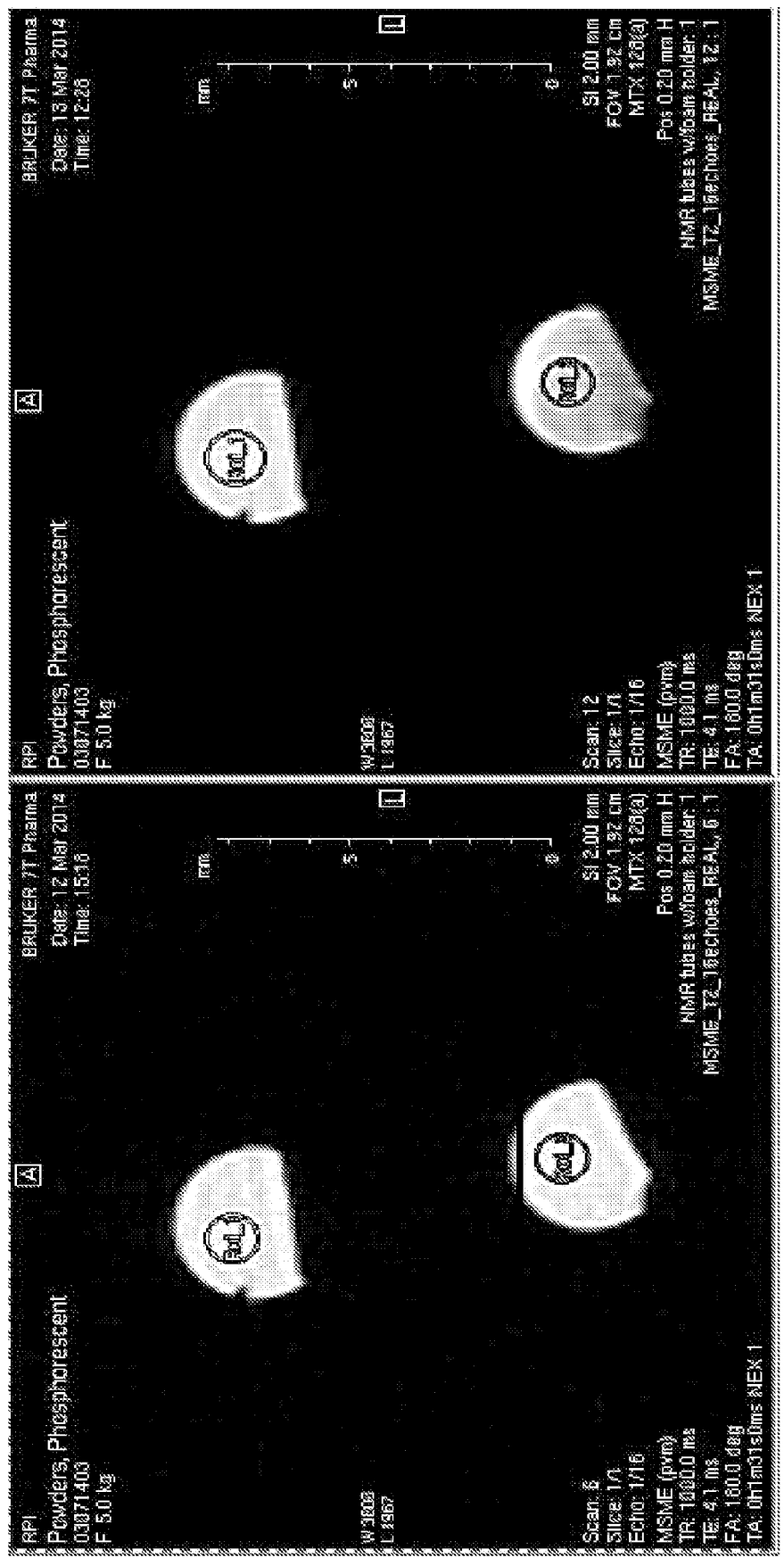
FIG. 8 shows an image of phosphorescent powders.

Table 1 shows the T2 times for the powders initially and after 20 hours. FIG. 7 shows the values from Table 1 in bar-graph form. Tube 1 was for the violet powder, and tube 2 was for the green powder. For each tube, the bar on the left represents the initial T2, and the bar on the right represents the T2 after 20 hours. Though a large difference was seen for the violet powder in particular, this was probably due to the stark difference from slurry to paste.

TABLE 1

T2 values for Example 1

| Tube Number | Tube Contents | T2 time @ t = 0 h | T2 time @ t = 20 h | Percent change |
|---|---|---|---|---|
| 1 | Violet Powder | 235.142 | 229.97 | 2.199522 |
| 2 | Green Powder | 225.767 | 16.6941 | 92.60561 |

Example 2

Figure 9:
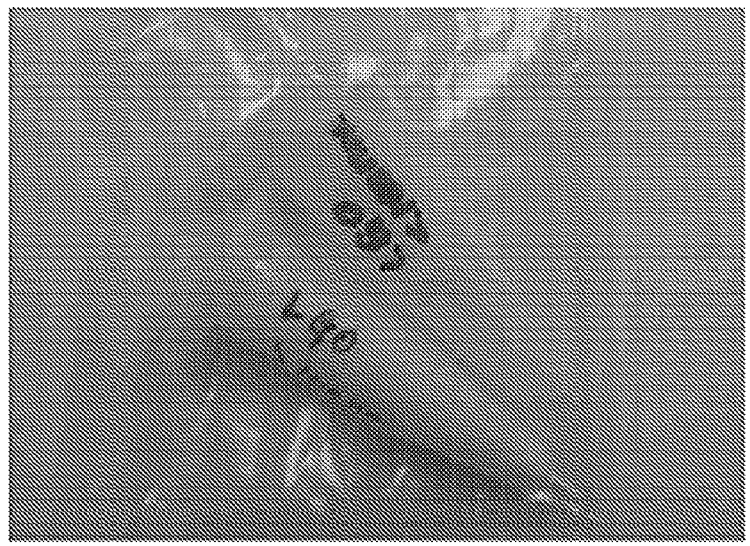
FIG. 9 shows an image of nanoparticles.
Figure 10:
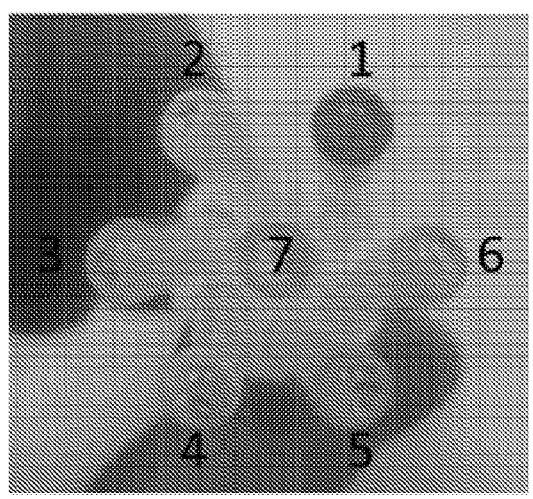
FIG. 10 shows an image of tubes having nanoparticles and tubes having water.
Figure 11:
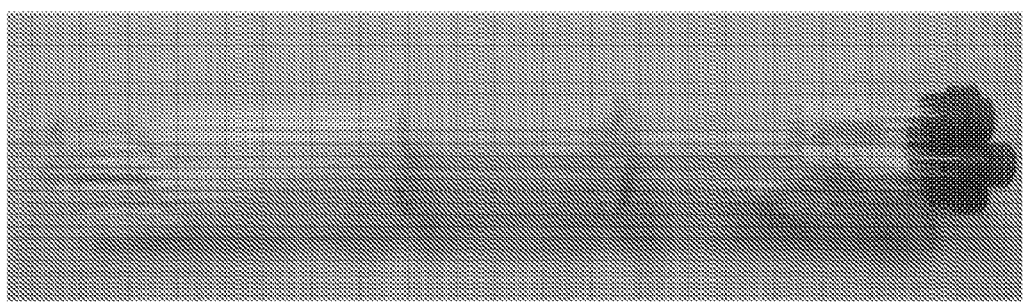
FIG. 11 shows an image of tubes having nanoparticles and tubes having water.

Nanoparticles at different densities were imaged. Five solutions having $LiGa_5O_8:Cr^{3+}$ nanoparticles at different concentrations were made using standard serial dilution methods. A first control of water doped with $CuSO_4$ and a second control of deionized water were also made. These seven samples were made in tubes, and are shown in FIGS. 9-11. The numerical labels are as follows: 1—control 1 (water doped with $CuSO_4$); 2—$LiGa_5O_8:Cr^{3+}$ nanoparticles at a density of 10 mg/mL; 3—$LiGa_5O_8:Cr^{3+}$ nanoparticles at a density of 5 mg/mL; 4—$LiGa_5O_8:Cr^{3+}$ nanoparticles at a density of 2.5 mg/mL; 5—$LiGa_5O_8:Cr^{3+}$ nanoparticles at a density of 1.25 mg/mL; 6—$LiGa_5O_8:Cr^{3+}$ nanoparticles at a density of 0.625 mg/mL; and 7—control 2 (deionized water). Tripilot scanning was used. Pre-excitement was performed by MSME (16 echoes), and T2 was measured (4.5 minutes). Micro-CT irradiation was performed at 45 kVp and 88 mA for 7.7 minutes. Tripilot was used again, and then post-excitement MSME (16 echoes was performed). The scale used to measure the particles had limited resolution, and the particles displayed poor solubility in the water, settling within 5 minutes. The micro-CT step experienced trouble with sample placement, and some samples fell out of the holder, leading to re-irradiation.

Figure 13:
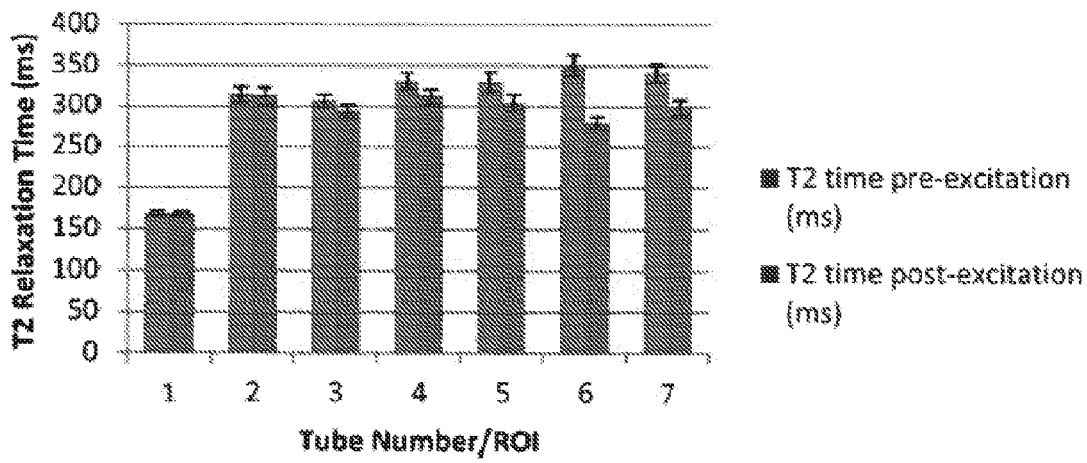
FIG. 13 shows a plot of $T_2$ relaxation time.
Figures 14A, 14B:
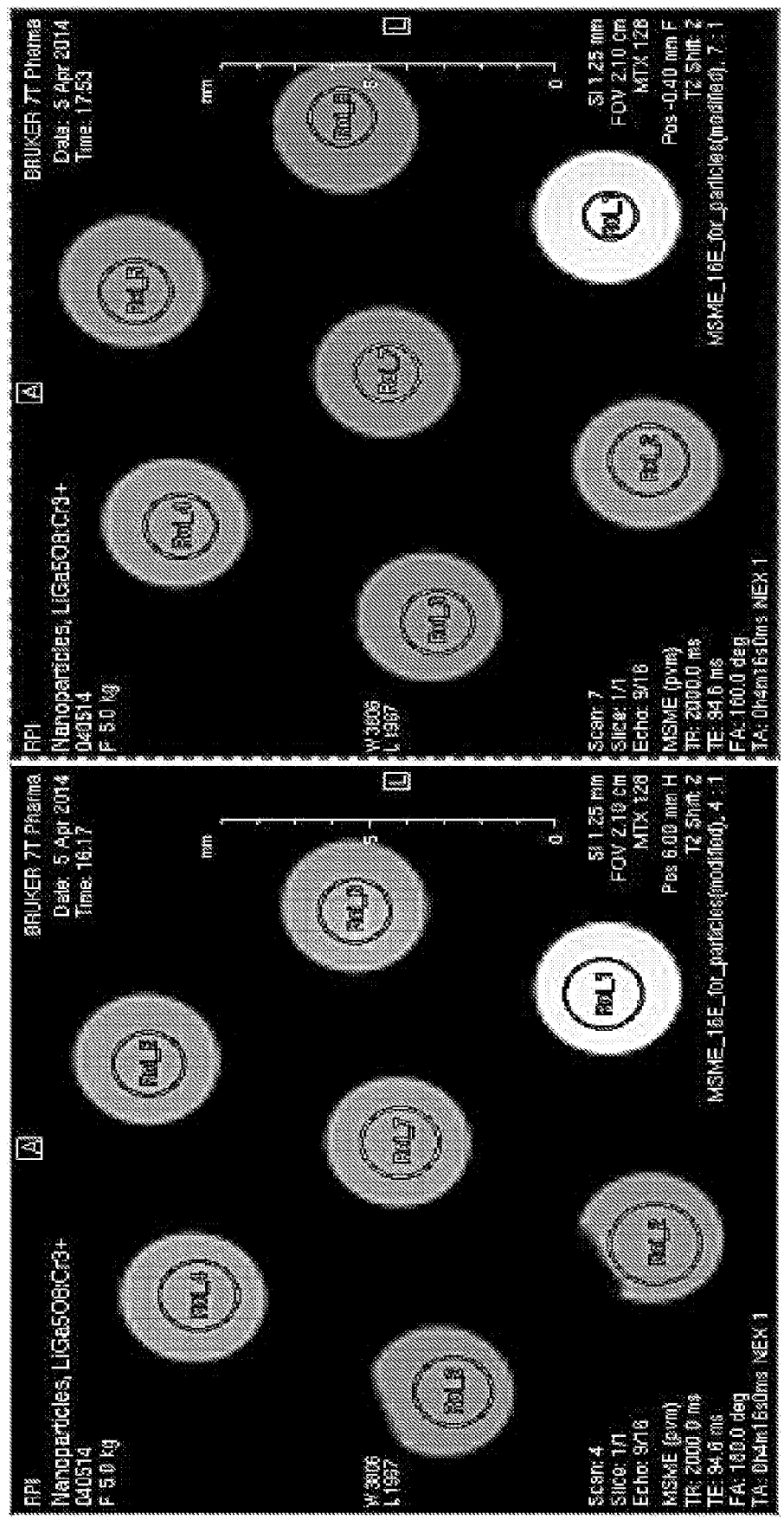
FIG. 14A shows an image of tubes having nanoparticles and tubes having water in a pre-excitation state.
FIG. 14B shows an image of tubes having nanoparticles and tubes having water in a post-excitation state.

Table 2 shows the T2 times for the samples pre-excitation and post-excitation (all T2 times are listed in milliseconds (ms)). FIG. 13 shows the values from Table 2 in bar-graph form. The tube numbers are displayed in Table 2 and, for each tube, the bar on the left represents the pre-excitation T2, and the bar on the right represents the post-excitation T2. FIG. 14 shows the MRI images of the tubes before (left side) and after (right side) excitation. Referring to Table 2 and FIG. 13, significant differences were observed in T2 before and after excitation. The trend is counterintuitive (i.e., unexpected) in that lesser concentrations of nanophosphors (NPs) show greater change. Control 2 (deionized water) also showed a significant change.

TABLE 2

T2 values for Example 2

| Tube Number | Tube Contents (NPs: LiGa5O8:Cr3+) | T2 pre-excitation (ms) | T2 post-excitation (ms) | Percent change |
|---|---|---|---|---|
| 1 | Doped water (CuSO4) | 169.246 | 168.861 | 0.23% |
| 2 | 10 mg/ml NPs | 314.073 | 312.743 | 0.42% |
| 3 | 5 mg/ml NPs | 306.306 | 294.43 | 3.88% |
| 4 | 2.5 mg/ml NPs | 330.856 | 311.922 | 5.72% |
| 5 | 1.25 mg/ml NPs | 329.828 | 304.1 | 7.80% |
| 6 | 0.625 mg/ml NPs | 350.332 | 279.744 | 20.15% |
| 7 | Deionized Water | 340.574 | 298.402 | 12.38% |

Example 3

Figure 15:
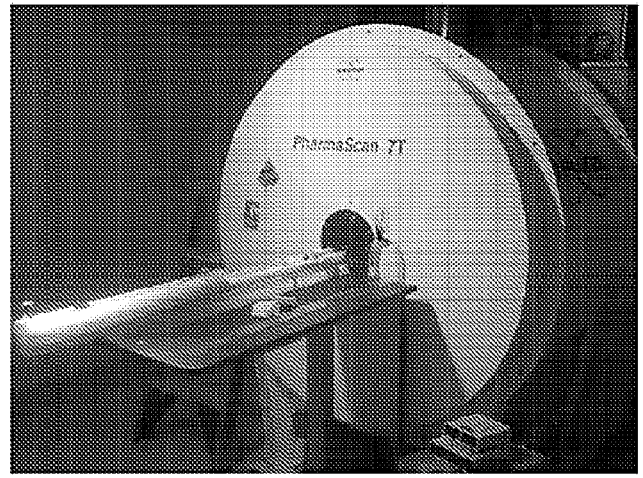
FIG. 15 shows an image of an MRI machine.
Figure 16:
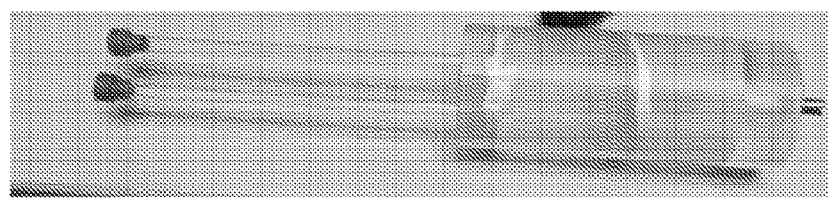
FIG. 16 shows an image of tubes having nanoparticles.
Figure 17:
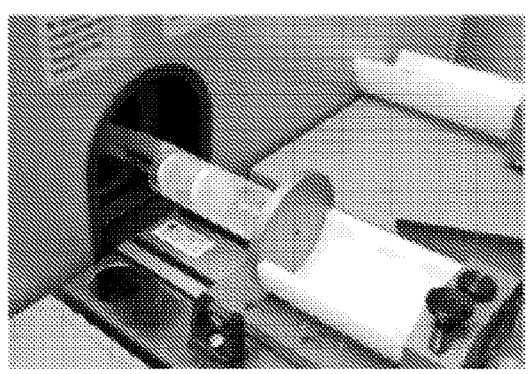
FIG. 17 shows an image of tubes having nanoparticles being inserted into an MRI machine.
Figure 18:
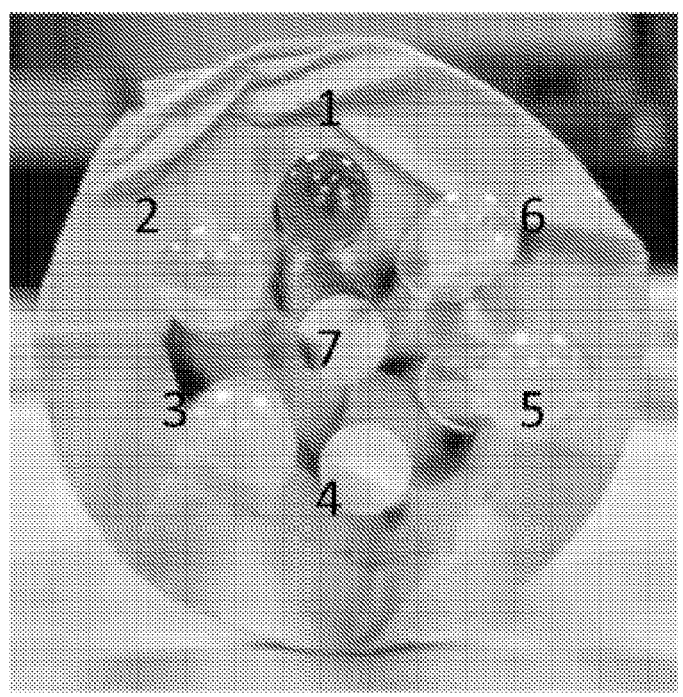
FIG. 18 shows an image of tubes having nanoparticles and tubes having water.

The same experiment from Example 2 was run again, only this time, the seven tubes were as follows: 1—control (water doped with $CuSO_4$); 2—$LiGa_5O_8:Cr^{34}$ nanoparticles at a density of 10 mg/mL (excited); 3—$LiGa_5O_8:Cr^{3+}$ nanoparticles at a density of 10 mg/mL; 4—empty; 5—$LiGa_5O_8:Cr^{3+}$ nanoparticles at a density of 10 mg/mL; 6—$LiGa_5O_8:Cr^{3+}$ nanoparticles at a density of 10 mg/mL (excited); and 7—empty. That is, the density of the $LiGa_5O_8:Cr^{3+}$ nanoparticles was the same in tubes 2, 3, 5, and 6, with tubes 2 and 6 having excited nanoparticles. FIG. 18 shows an axial image of tubes 1-7. FIGS. 15-17 show images of equipment used in this experiment. A more sensitive scale was used compared to that used in Example 2. The particles again settled within 5 minutes. The T2 measurements varied greatly within each sample depending on ROI location (NPs settled on bottom versus water in center).

Figure 19:
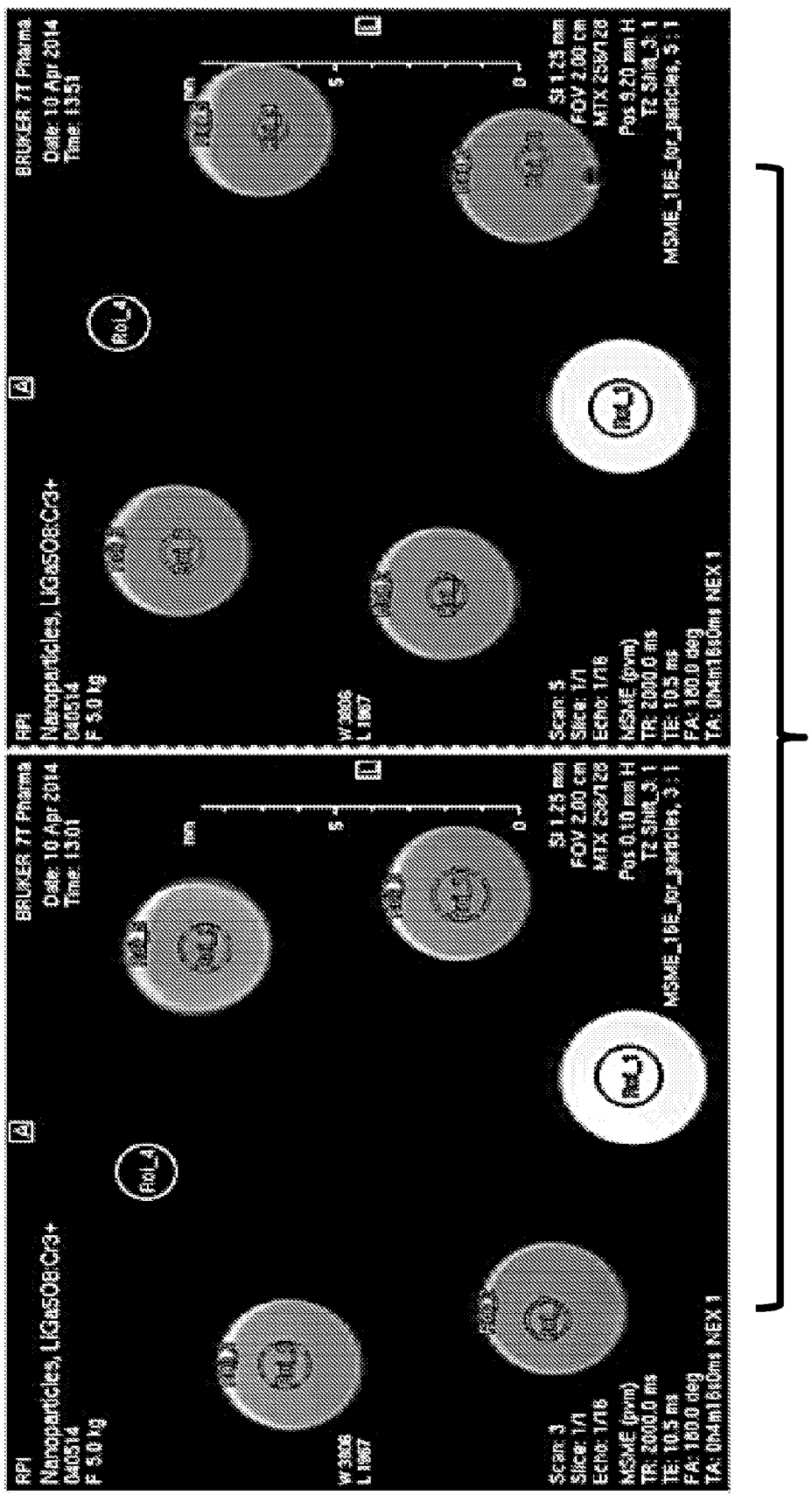
FIG. 19 shows images of tubes having nanoparticles and tubes having water.
Figure 20:
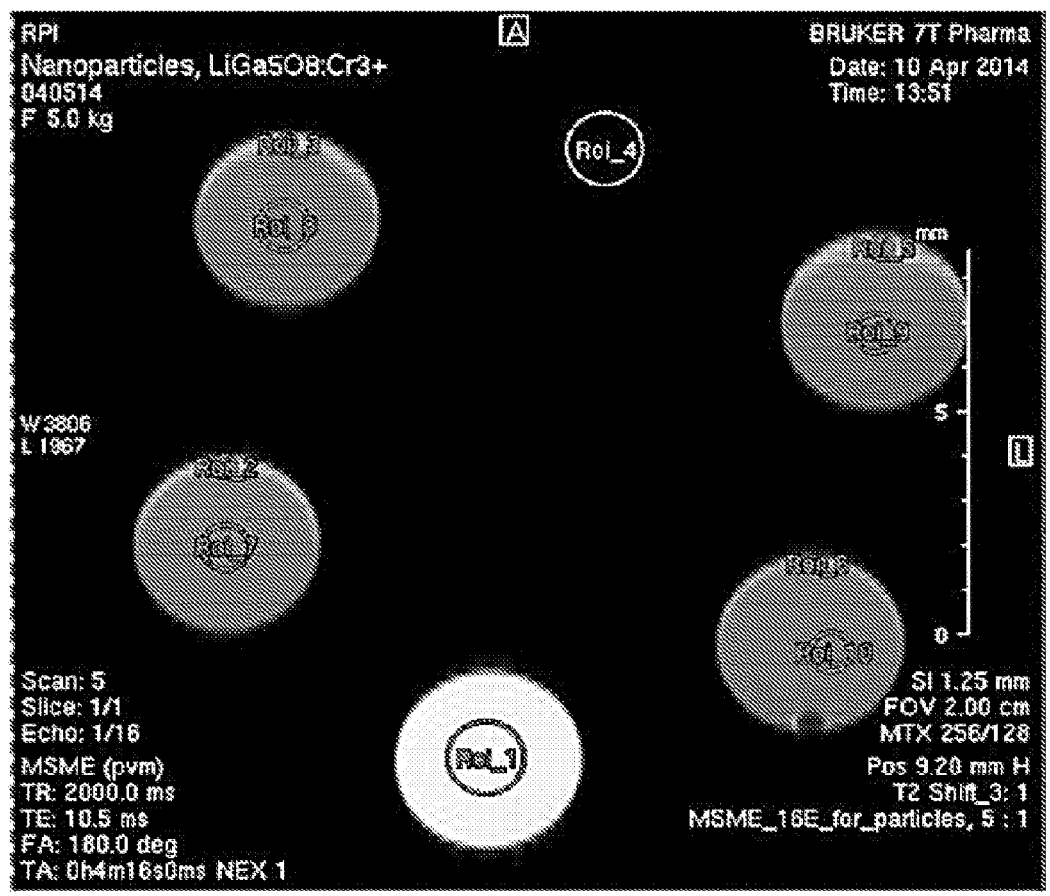
FIG. 20 shows an image of tubes having nanoparticles and tubes having water.
Figure 21A:
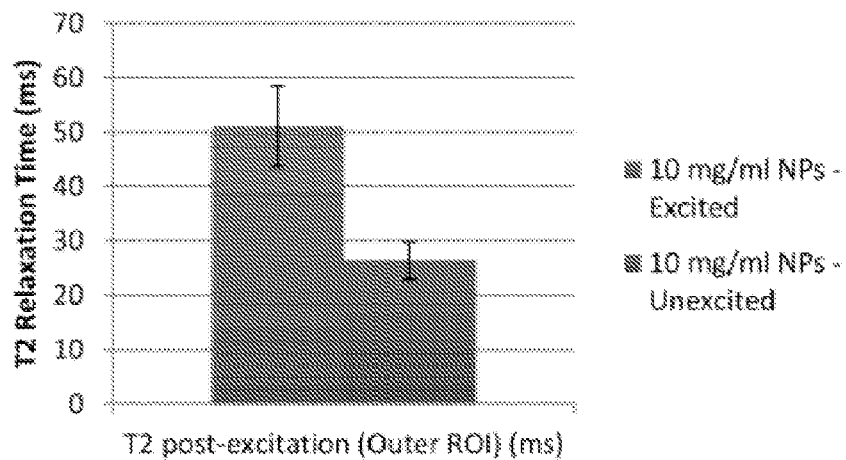
FIG. 21A shows a plot of $T_2$ relaxation time for settled nanoparticles.
Figure 21B:
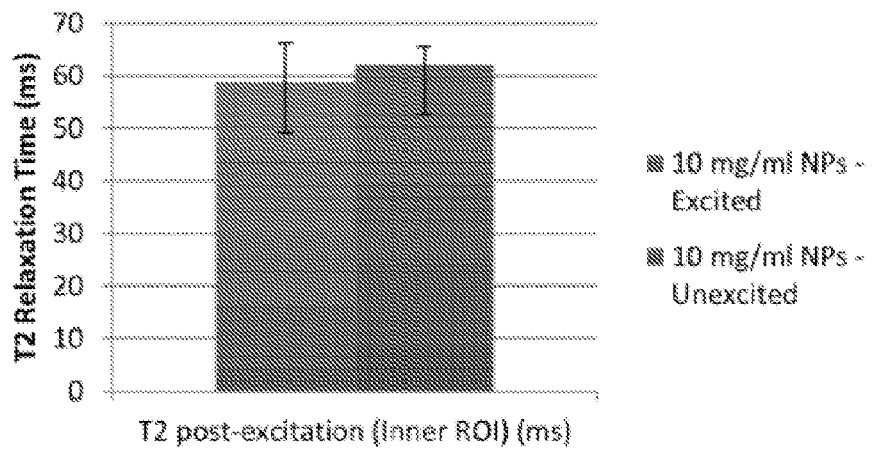
FIG. 21B shows a plot of $T_2$ relaxation time for bulk water.

Table 3 shows the T2 times for the samples pre-excitation (outer ROI), pre-excitation (inner ROI), post-excitation (outer ROI), and post-excitation (inner ROI) (all T2 times are listed in microseconds (ms)). FIG. 19 shows MRI images of the tubes. FIG. 21A shows a bar graph of the T2 relaxation time for an outer ROI for 10 mg/mL excited NPs (left bar) and 10 mg/mL unexcited NPs (right bar); this is for settled particles. FIG. 21B shows a bar graph of the T2 relaxation time for an inner ROI for 10 mg/mL excited NPs (left bar) and 10 mg/mL unexcited NPs (right bar); this is for bulk water. FIG. 20 shows an MRI image with outlining for the ROI used for the date in FIGS. 21A and 21B.

Figure 22:
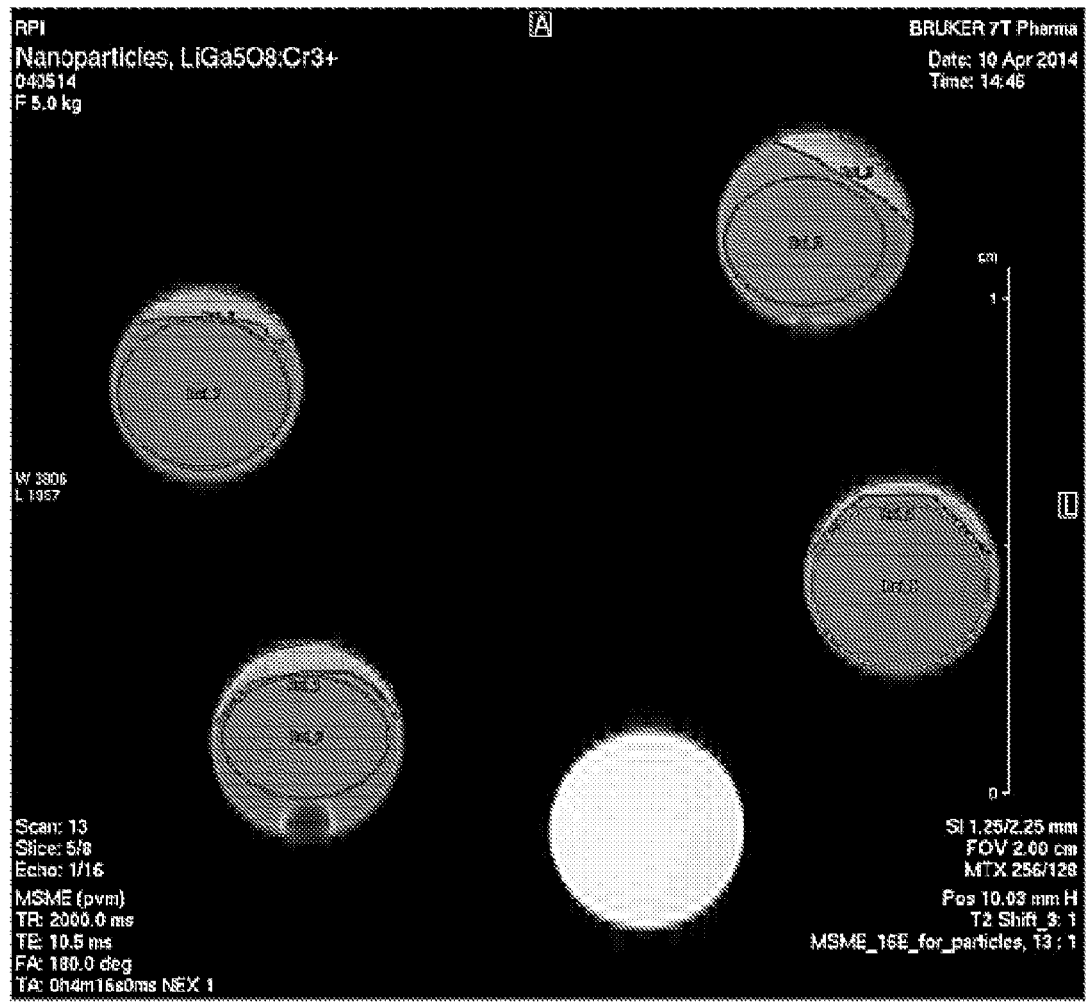
FIG. 22 shows an image of tubes having nanoparticles and tubes having water.
Figure 23A:
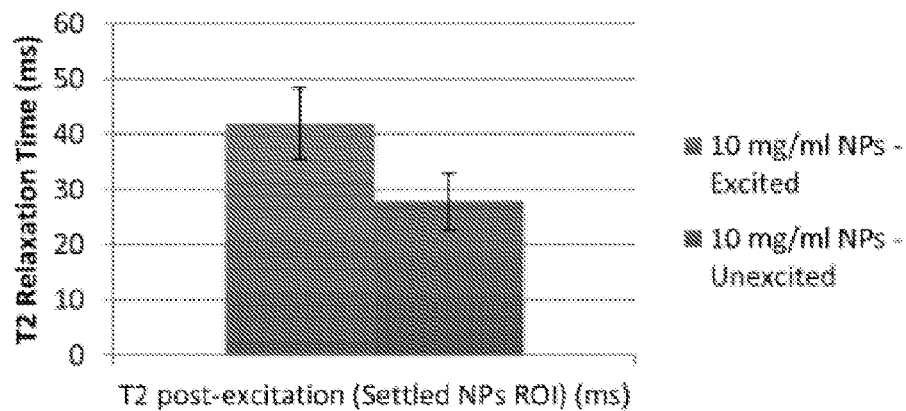
FIG. 23A shows a plot of $T_2$ relaxation time for settled nanoparticles.
Figure 23B:
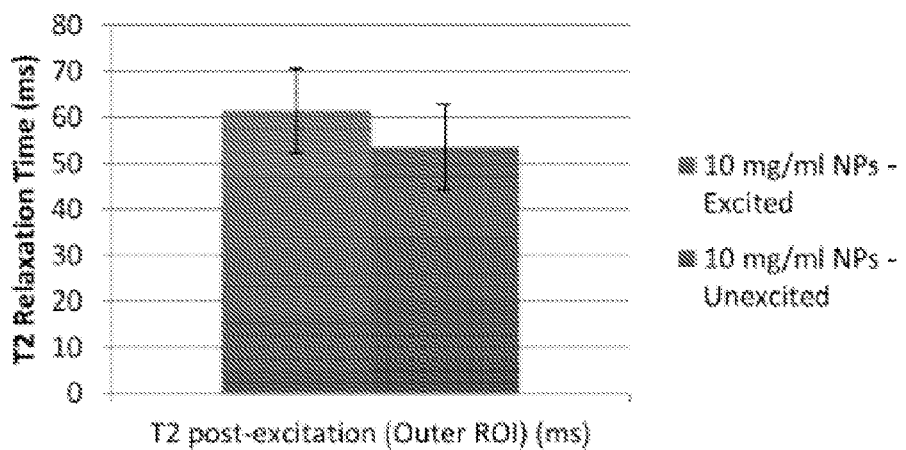
FIG. 23B shows a plot of $T_2$ relaxation time for bulk water.
Figure 24:
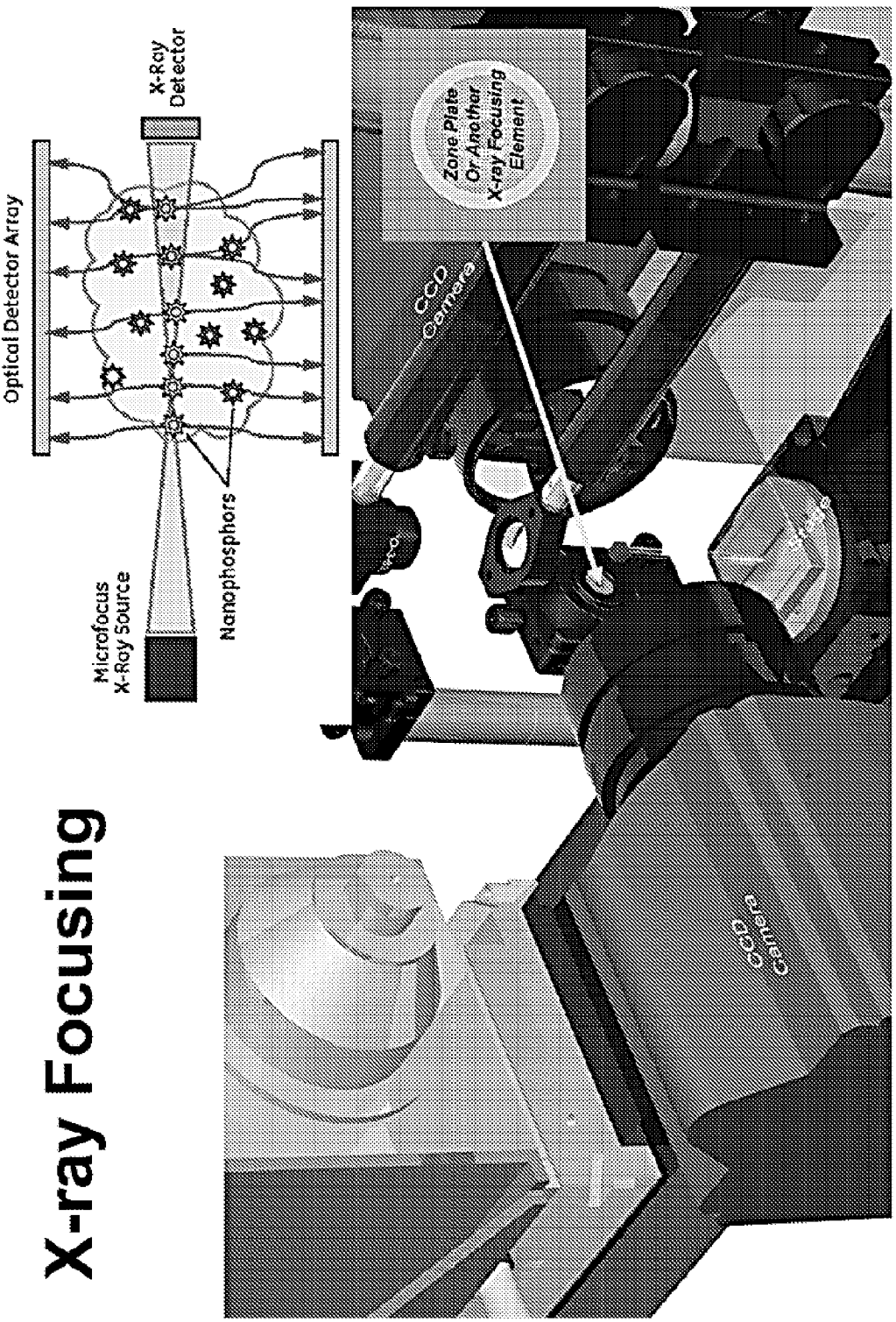
FIG. 24 shows a schematic view of a system according to an embodiment of the subject invention.
Figure 25A:
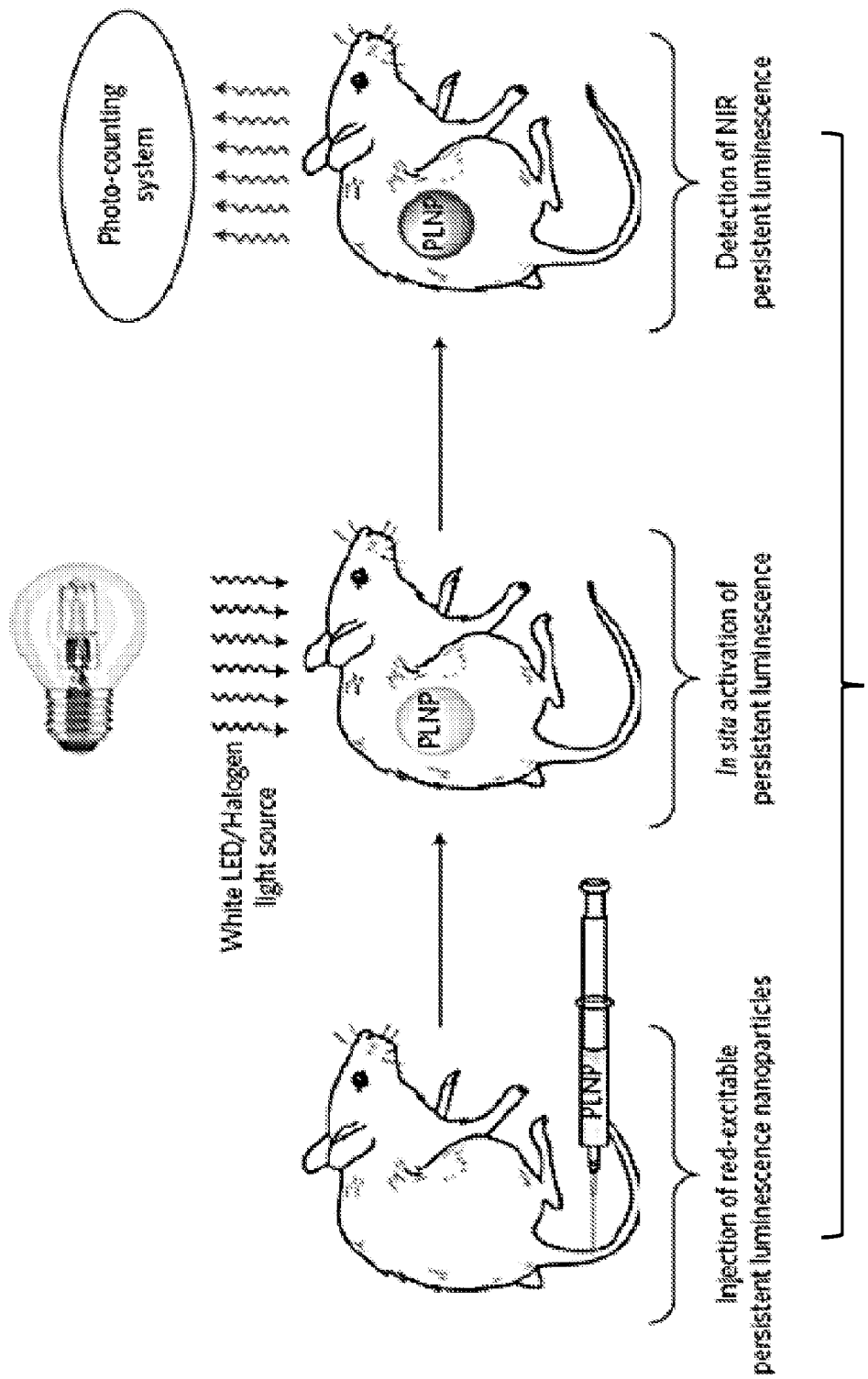
FIG. 25A shows a scheme demonstrating persistent nanophosphors.
Figure 25B:
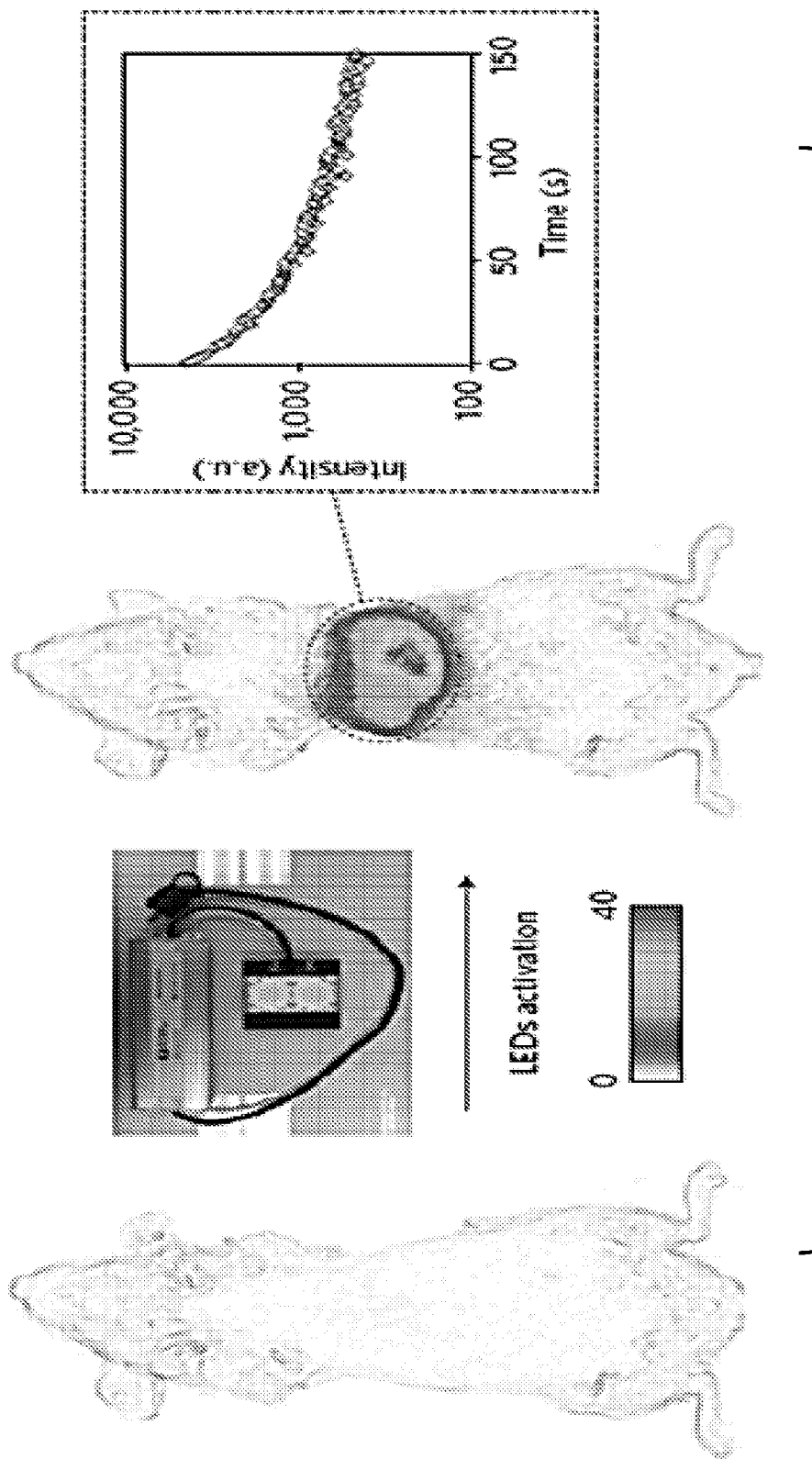
FIG. 25B shows a scheme demonstrating persistent nanophosphors.
Figure 26:
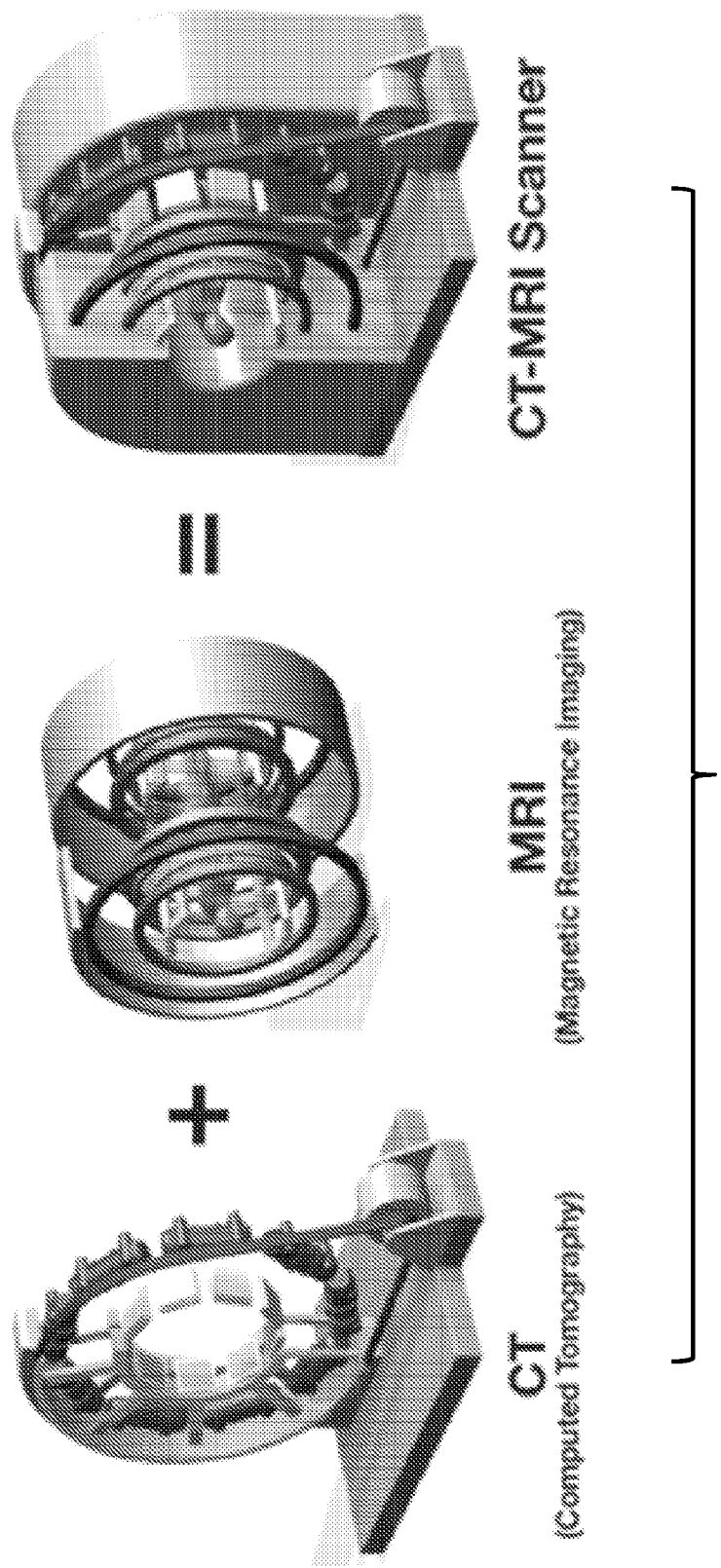
FIG. 26 shows a schematic view of a combined computed tomography-magnetic resonance imaging (CT-MRI) scanner according to an embodiment of the subject invention.
Figure 27:
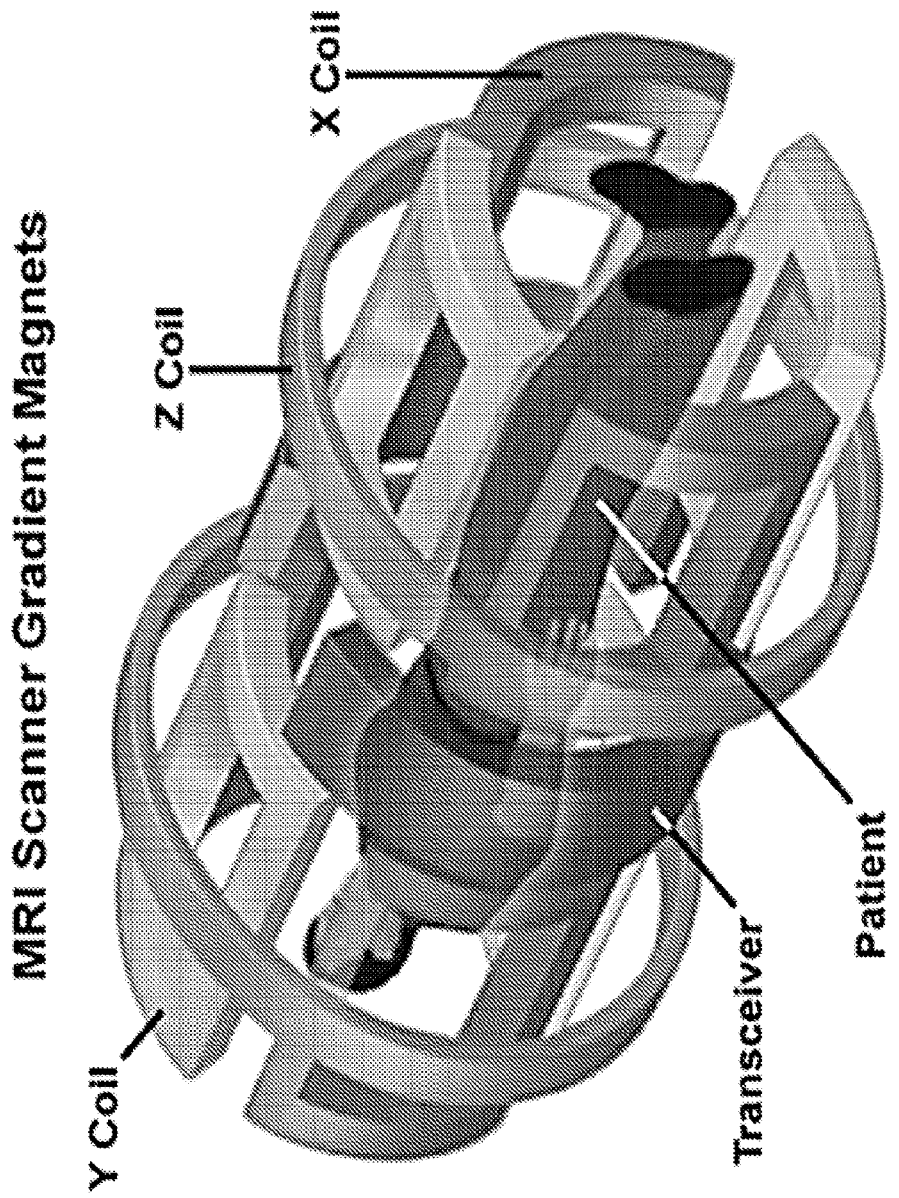
FIG. 27 shows an image of gradient coils of an MRI scanner.
Figure 28:
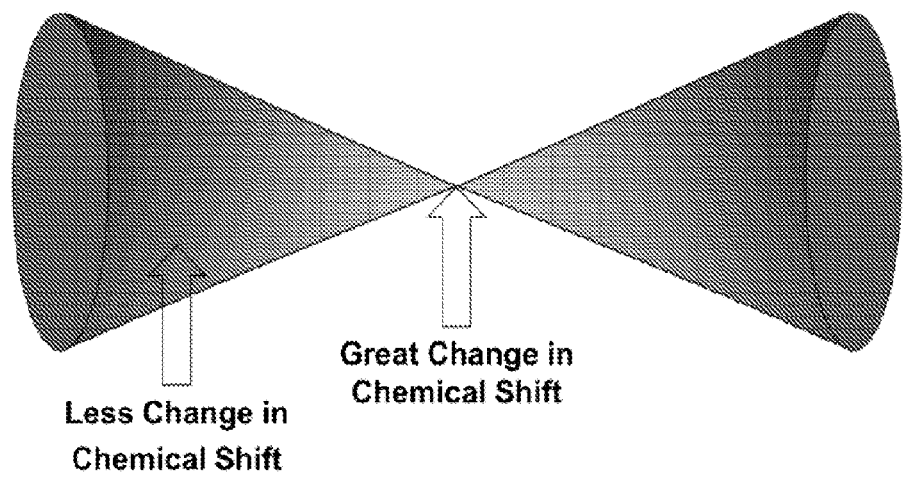
FIG. 28 shows an image of modulated X-rays for localization.
Figure 29:
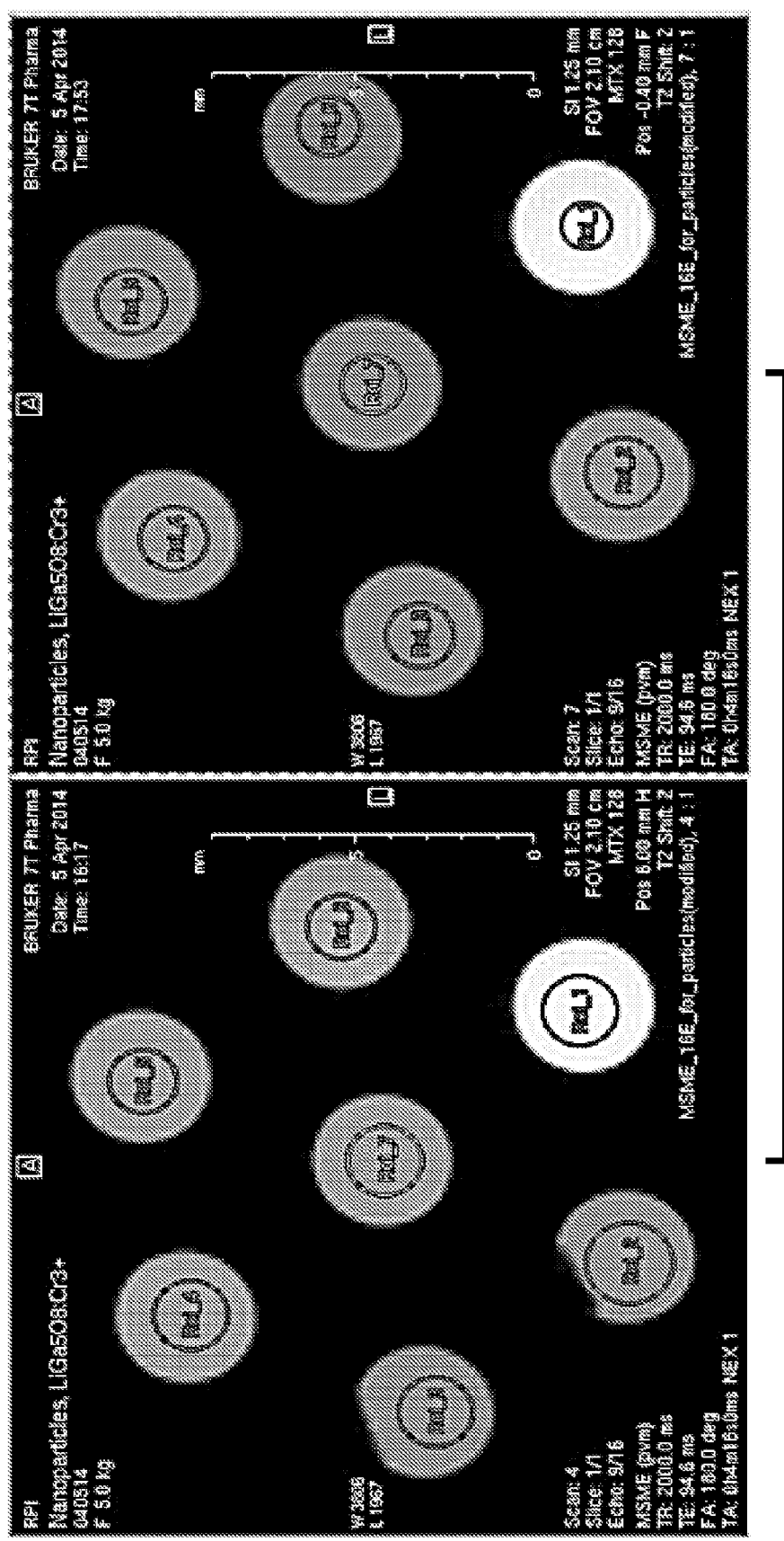
FIG. 29 shows images of nanoparticles within tubes.
Figures 32A, 32B, 32C:
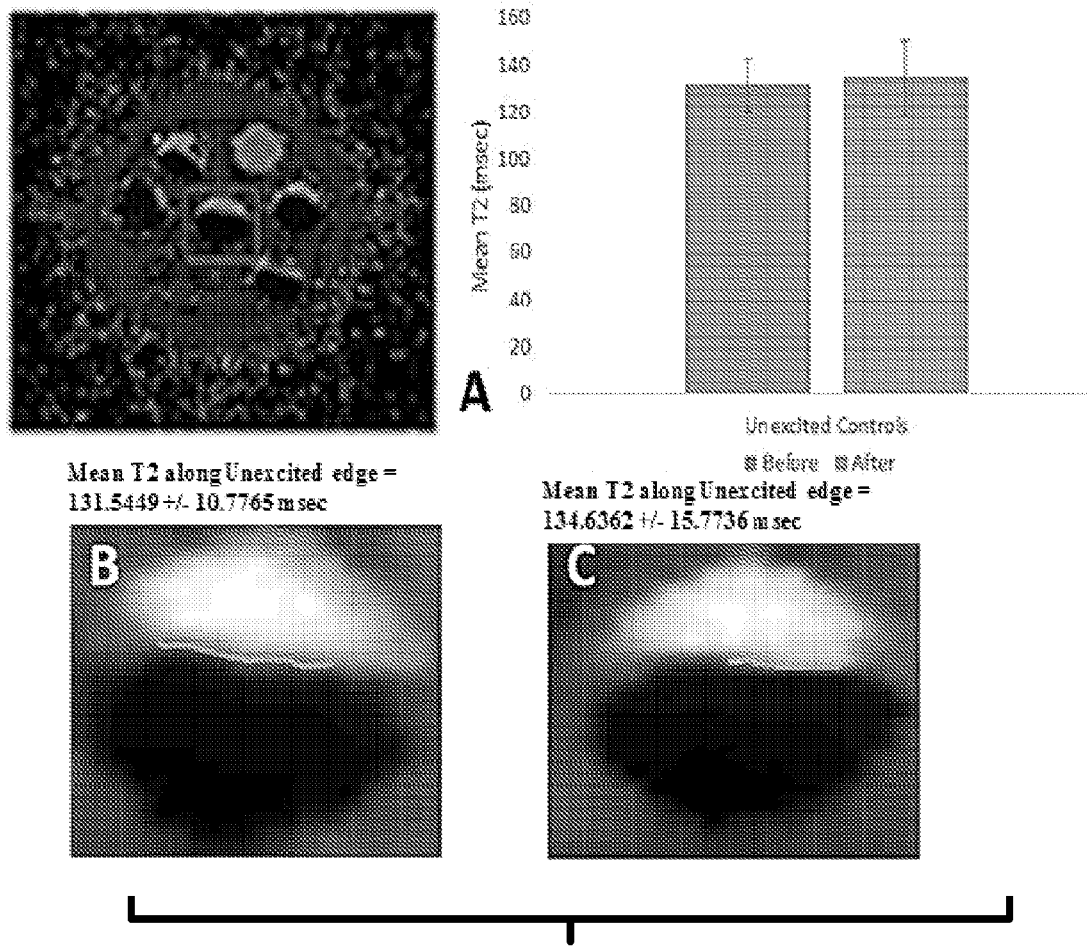
FIG. 32A shows an image of nanophosphors and a bar graph showing mean $T_2$ relaxation time.
FIG. 32B shows an image of a control sample before excitation.
FIG. 32C shows an image of the control sample of FIG. 32B after excitation.

FIG. 23A shows a bar graph of the T2 relaxation time for settled NPs ROI for 10 mg/mL excited NPs (left bar) and 10 mg/mL unexcited NPs (right bar). FIG. 23B shows a bar graph of the T2 relaxation time for an outer ROI for 10 mg/mL excited NPs (left bar) and 10 mg/mL unexcited NPs (right bar); this is for bulk water. FIG. 22 shows an MRI image with outlining for the ROI used for the date in FIGS. 23A and 23B.

The X-ray excited samples were prepared in a Scanco vivaCT 40 and scanned at a tube voltage of 70 kVp and tube current of 114 μA. The pitch and number of projections were set to have the scan run for at least 15 minutes according to the imaging software.

The UV excited samples were prepared on the bottom of a Spectrolinker XL-1000 device, which produces UV radiation at 254 nm, 2 A, and 120 V. The samples were irradiated for 15 minutes.

To verify the persistent luminescence from the nanophosphors, preliminary observations were made by Nikon TE2000 wide-field microscopy (invertedepi-fluorescence

TABLE 3

T2 values for Example 3

| Tube Number | Tube Contents | T2 pre-excitation (Outer ROI) (ms) | T2 pre-excitation (Inner ROI) (ms) | T2 post-excitation (Outer ROI) (ms) | T2 post-excitation (Inner ROI) (ms) | Percent Change (Outer ROI) | Percent Change (Inner ROI) |
|---|---|---|---|---|---|---|---|
| 1 | Doped water (CuSO4) |  | 126.683 |  | 120.208 |  | 5.11% |
| 2 | 10 mg/ml NPs - Excited | 54.8117 | 61.6567 | 44.195 | 52.8227 | 19.37% | 14.33% |
| 6 | 10 mg/ml NPs - Excited | 34.022 | 53.0842 | 57.9258 | 64.7838 | 70.26% | 22.04% |
| 3 | 10 mg/ml NPs | 19.5639 | 43.385 | 31.786 | 72.6739 | 62.47% | 67.51% |
| 5 | 10 mg/ml NPs | 25.3117 | 81.3098 | 21.0454 | 51.6328 | 16.86% | 36.50% |

Example 4

All the nanophosphors used were $LiGa_5O_8:Cr^{3+}$ nanophosphors having a size of <100 nm. These particles are highly non-colloidal, settling out of an aqueous solution within 2 minutes. Long-term settling (>1 hour) resulted in hypo-intense regions within the MRI images indicative of a lack of hydrogen molecules to give readable MRI signals. For this reason, the samples had to be agitated before each set of acquisitions and excitations. This resulted in decreased control over the particle distribution within any given sample between before- and after-excitations.

The measured phosphor content in each sample through bulk concentration calculations may have been misrepresentative of the true local concentrations that resulted from the quick settling behavior of the nanophosphors when placed in water. Thus, small amounts of "dispersed" nanophosphors were added in water to a 3 mm diameter capillary tube. After the particles visibly settled, the supernatant water was removed from the sample and more "dispersed" nanophosphors were added to the sample. This stepwise addition of nanophosphors continued until the capillary tube had approximately a 7-mm tall column of nanophosphors. After the required volume was achieved, the remaining supernatant was kept on top of the net volume of nanophosphors to be used as the proton source for all MRI measurements.

Two samples were made for each trial (X-ray excited, UV excited, unexcited nanophosphors). The unexcited samples were not subjected to any X-ray excitation during the experiments. Hereafter the scans of this example are referred to as either "before-excitation" or "after-excitation" to distinguish the two time points of the scans even though not all samples in the "after-excitation" scan underwent excitation. Additionally, a capillary tube was filled with water to serve as a reference. The seven capillary tubes were then arranged in a hexagonal shape, wrapped into a bundle with parafilm, and placed in a small polystyrene tube surrounded by Cu2SO4-doped water. FIGS. 30A and 30B show side and axial views, respectively, of the capillary tube arrangement (can be referred to as the phantom arrangement) in a polystyrene holder. FIG. 30C shows the specific placement of the samples as placed in the MRI imager.

mode; 4× objective lens) with an emission filter (bandwidth 60 nm at 720 nm, Chroma). The microscope was housed in a transparent plastic chamber, in which a "dark-room" was created by black-cloth coverage. For homogenous close-up stimulation, the continuous-wave laser stimulation source at 635 nm (single-mode semiconductor CW laser, S1FC635, Thorlabs) was coupled to a fiber cable (OceanOptics) and a megapixel ultra-low-distortion compound lens (⅔", 25 mm, C-mount, M2518-MPW2, Computer). The laser stimulation power was set at 2 mW for each exposure time of 5 seconds.

The respective phantoms were placed in a Bruker 13 cm, 7T horizontal bore MRI scanner, centered in a 23 mm RF coil. Special care was taken to preclude air bubbles that were present in the regions to be imaged. Prior to the T2 experiments, the position of each phantom was optimized and established using a gradient echo TriPilot scan. The local magnetic field about the field of view (FOV) was further optimized using the FieldMap routine. The T2 experiments consisted of a multi-spin, multi-echo protocol in which the echo times (TEs) were varied as a train of 16 equally spaced echoes of 10.5 msec with a repetition time (TR) of 2000 msec. The FOV was 20 mm×20 mm with an in-plane resolution of 0.156 mm×0.156 mm and slice thickness of 1.25 mm. Six slices were taken to collect as many usable image data as possible. These parameters led to a scan time of 2 minutes and 13 seconds. The resulting dataset from a T2 experiment was processed as a 4-D matrix with dimensions of 128×128×6×16 (x, y, z, TE) whose voxel values represent signal intensity modeled by Equation 1:

$$S = k\rho\left(1 - \exp\left(-\frac{TR}{T_1}\right)\right)\exp\left(-\frac{TE}{T_2}\right), \qquad (1)$$

where S is the amplitude of the signal, k is a proportionality constant that depends on the machine and RF coil, the unknown $T_1$, $T_2$ (same as T2), and ρ (proton density) can be imaged at will.

The 4-D dataset was pixel-wise fit into Equation 2 across the TE dimension using the Image Sequence Analysis tool of the ParaVision software (v5.1) as supplied by Bruker:

$$S = A\exp\left(-\frac{TE}{T_2}\right) + c. \quad (2)$$

Equation 2 is a simplified version of Equation 1 with A being the machine specific proportionality constant k multiplied by the sample specific constant ρ (proton density) and the $(1-\exp(-TR/T_1))$ function, since TR was held constant in the experiment. The resulting dataset from this analysis step is a 3-D matrix with dimensions of 128×128×6, and can be referred to as the $T_2$ map. This dataset was further reduced by manual selection of the slice that contained the largest number of usable samples. Samples were considered usable when a clear interface could be seen between the nanophosphor and water regions. Because of this restriction, one UV excited sample and one unexcited sample were excluded from the analysis because none of the slices contained a usable interface. An additional output from the ParaVision $T_2$ mapping software is the intensity image that was also used as the proton-density-weighted image, although it is more representative of the image of the raw intensities at the first TE.

Taking into account the nanophosphor settling as well as the inner- and outer-sphere relaxation mechanisms of contrast agents modeled by Solomon-Bloembergen-Morgan (SBM) relaxation theory, the change in $T_2$ relaxation may be found at the interface between the nanophosphor and water in the samples. Analysis of the interface was conducted using common image processing and segmentation algorithms including interpolation, Otsu thresholding, and Sobel edge detection. Some manual intervention was also used to select ROIs and choose the edges found to be representative of the nanophosphor-water interface. All of these techniques were implemented in a customized MATLAB code.

Figure 33:
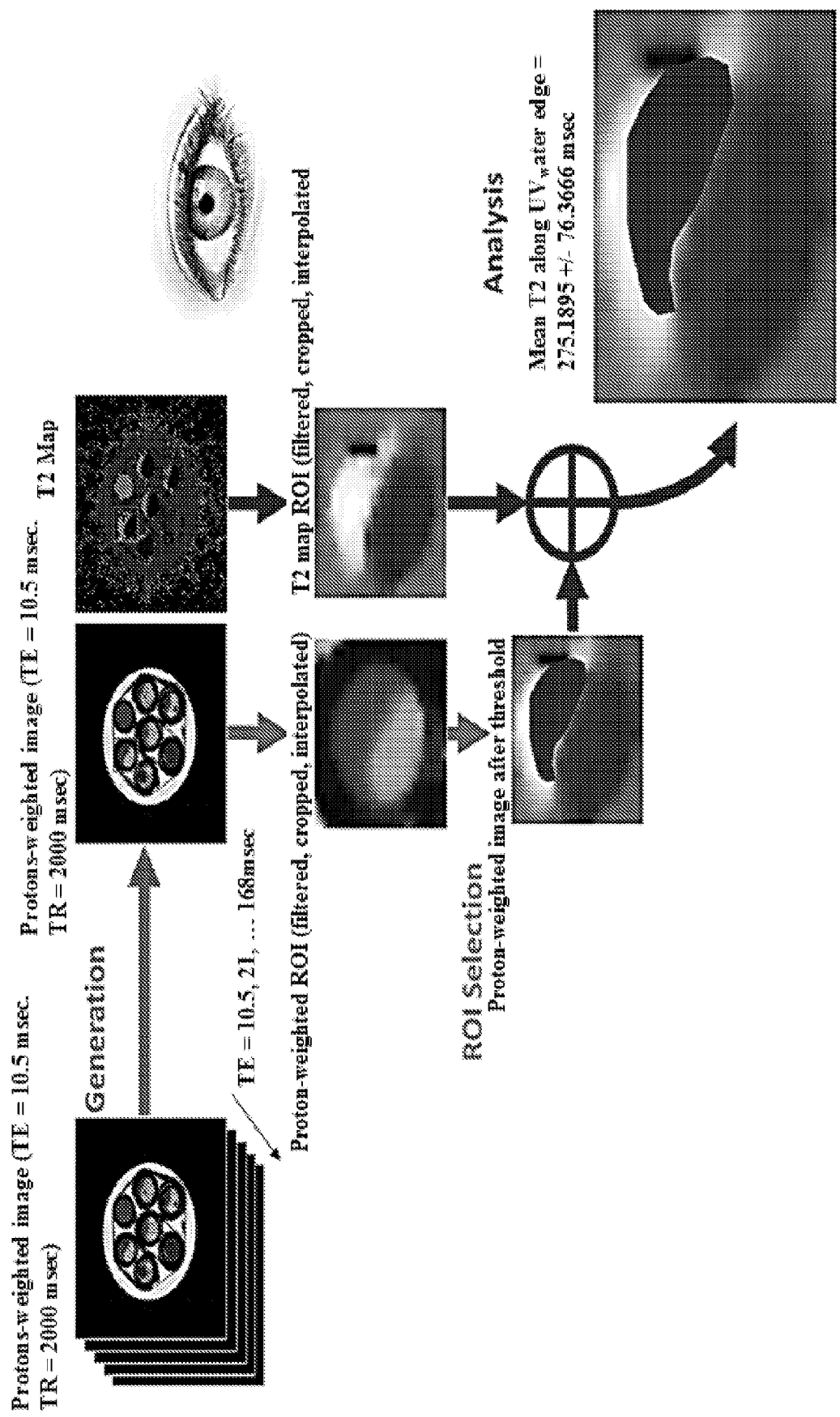
FIG. 33 shows a diagram of image analysis according to an embodiment of the subject invention.
Figures 34A, 34B, 34C:
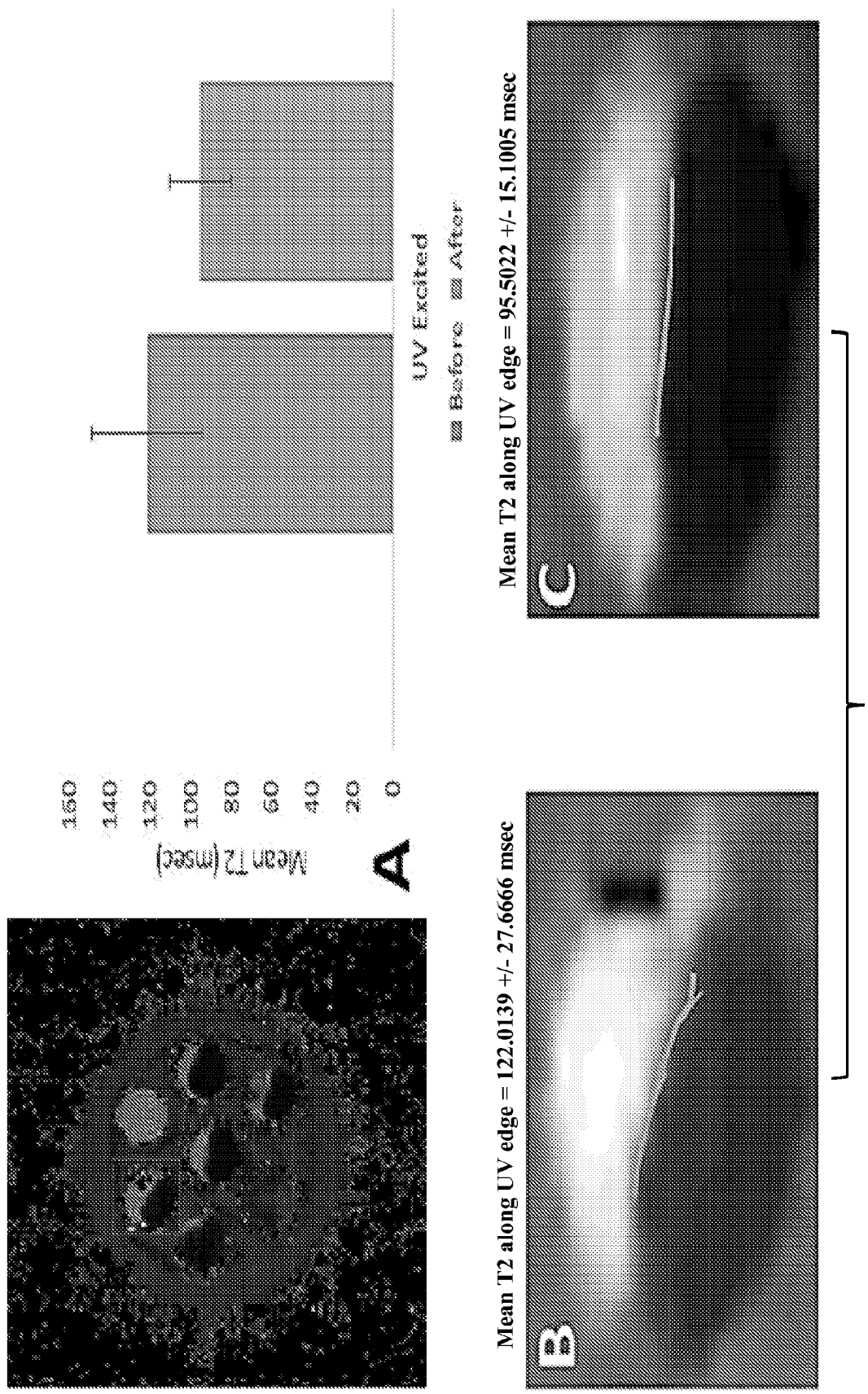
FIG. 34A shows an image of nanophosphors and a bar graph showing mean $T_2$ relaxation time.
FIG. 34B shows an image of a sample before excitation.
FIG. 34C shows an image of the sample of FIG. 34B after excitation.
Figures 35A, 35B, 35C:
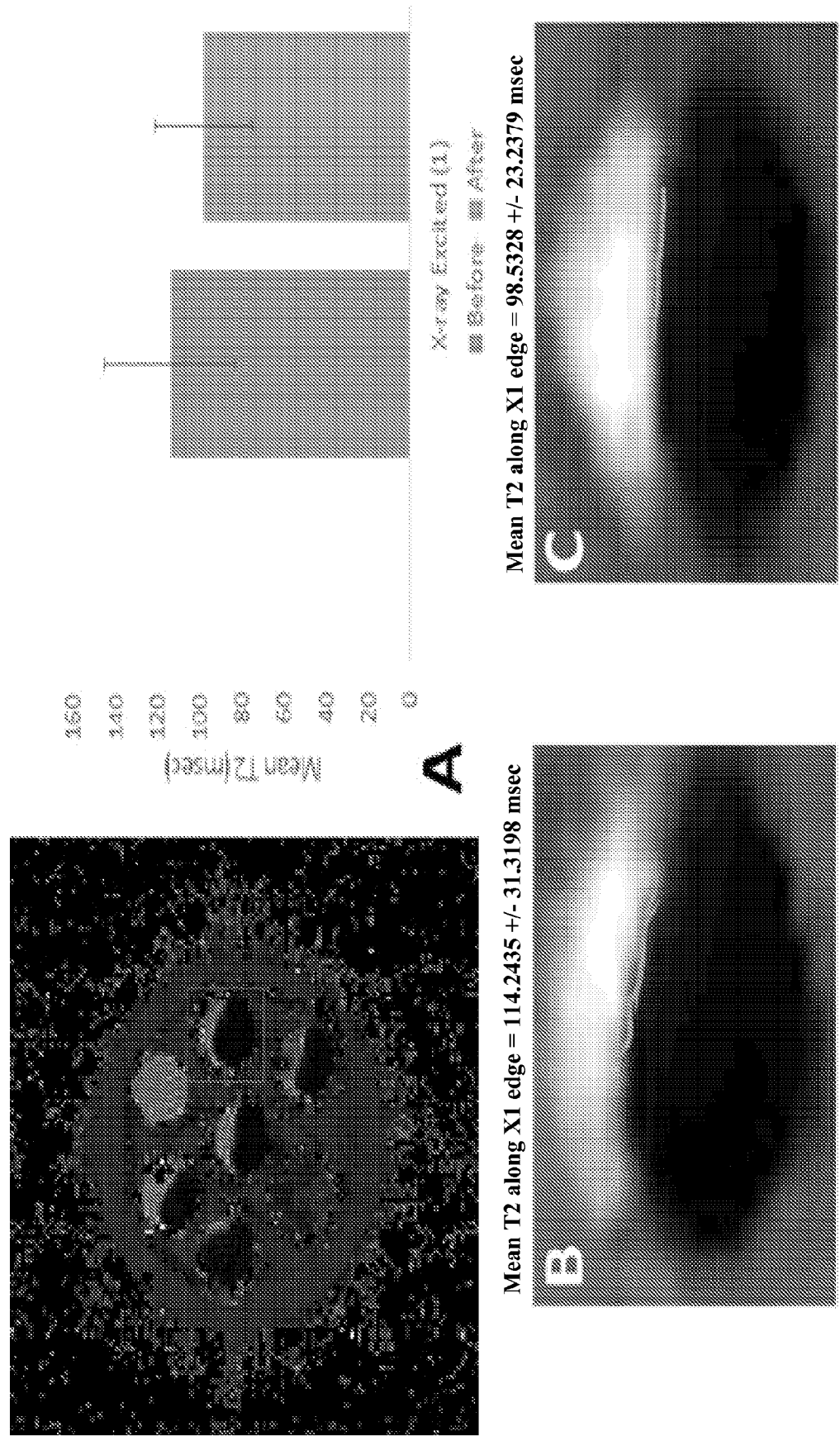
FIG. 35A shows an image of nanophosphors and a bar graph showing mean $T_2$ relaxation time.
FIG. 35B shows an image of a sample before excitation.
FIG. 35C shows an image of the sample of FIG. 35B after X-ray excitation.
Figures 36A, 36B, 36C:
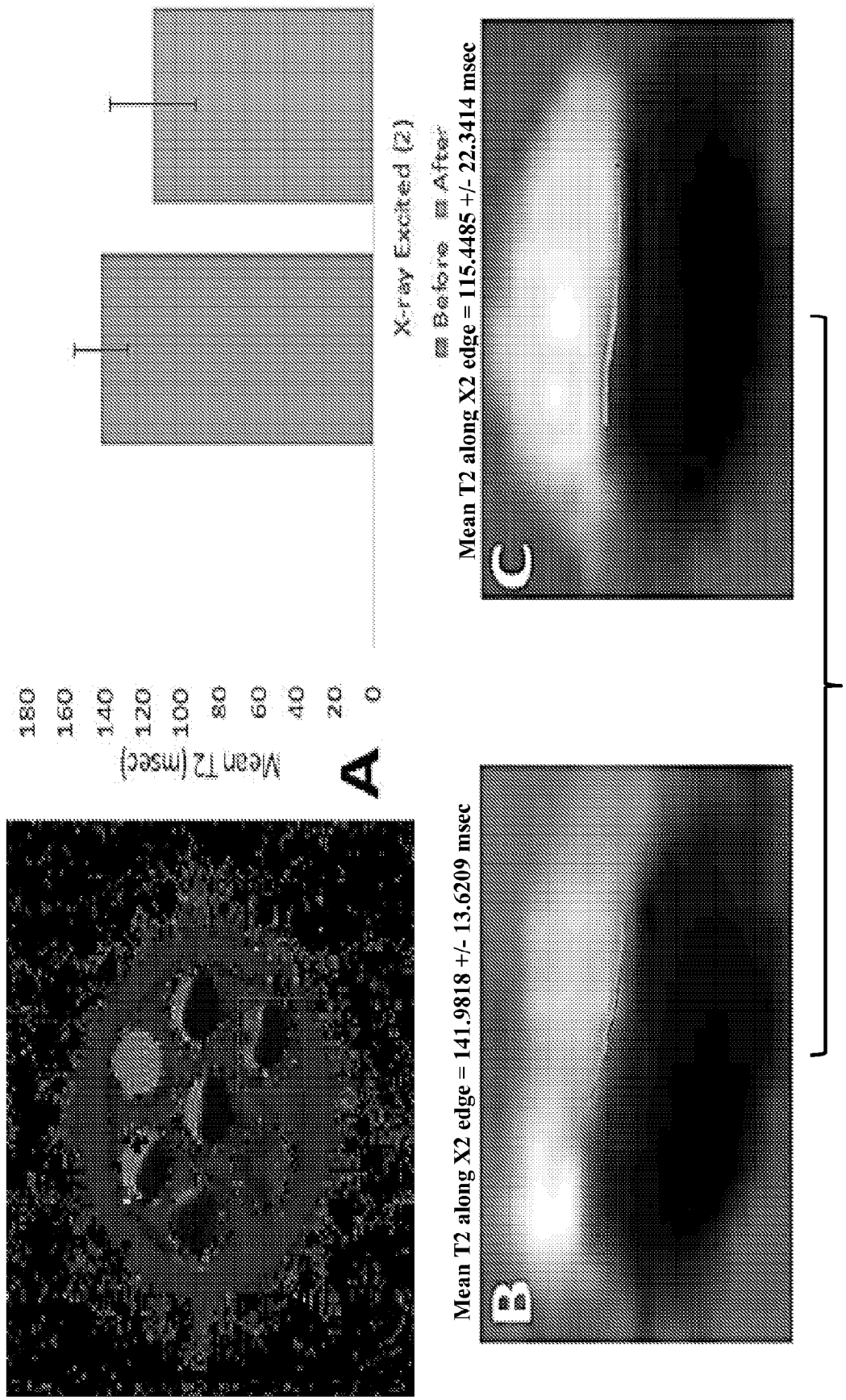
FIG. 36A shows an image of nanophosphors and a bar graph showing mean $T_2$ relaxation time.
FIG. 36B shows an image of a sample before excitation.
FIG. 36C shows an image of the sample of FIG. 36B after X-ray excitation.

The Otsu thresholding and Sobel edge detection were performed on the proton-density-weighted ROIs. This outcome was treated as the "true" interface between nanophosphor deposit and water. Once the edges were identified, they were mapped to the $T_2$ image, and the values from the pixels along the edge were averaged. To reduce the measurement error, edges were manually restricted to the areas of qualitative contrast between nanophosphors and water. FIG. 33 shows a diagram of the workflow of data analysis. This same pipeline was repeated four more times for each sample adjusting the Otsu threshold value by 2 grayscale units in both the water (Threshold−value) and NP (Threshold+value) directions to test the robustness of the data trends.

FIGS. 31A and 31B show the microscopy images with laser stimulation off and on, respectively. The laser stimulation on-off observations were repeated several times with the NPs sample intentionally exposed to the room-light illumination between each trial. The persistent luminescence was subject to negligible leakage under room-light illumination while the CW laser illumination could effectively stimulate the release of the stored UV energy for narrow-band luminescence re-emissions at 716 nm.

FIGS. 32 and 34-36 show comparison of mean T2 time constants along the water-NP interface before excitation and after excitation. FIGS. 32A, 34A, 35A, and 36A each shows an image of nanophosphors and a bar graph showing mean T2 relaxation time. In each of FIGS. 32A, 34A, 35A, and 36A, the left bar is before excitation and the right bar is after excitation. FIGS. 32B, 34B, 35B, and 36B each shows an image of the sample before excitation, and FIGS. 32C, 34C, 35C, and 36C each shows an image of the sample from FIGS. 32B, 34B, 35B, and 36B, respectively, after excitation.

Referring to FIGS. 32 and 34-36, an effect from excitation is suggested. In each of the excited samples (UV—FIG. 34, X-ray1—FIG. 35, X-ray2—FIG. 36), a decrease in mean T2 is possibly evident although the standard deviations overlap. The unexcited control (FIG. 32), however, shows a slight but insignificant increase in mean T2 along the edge as seen in FIG. 32. With this control in mind, excitation of the nanoparticle slurries via UV and X-ray seem to show a trend toward a decreased T2 after excitation relative to before excitation.

Figure 37:
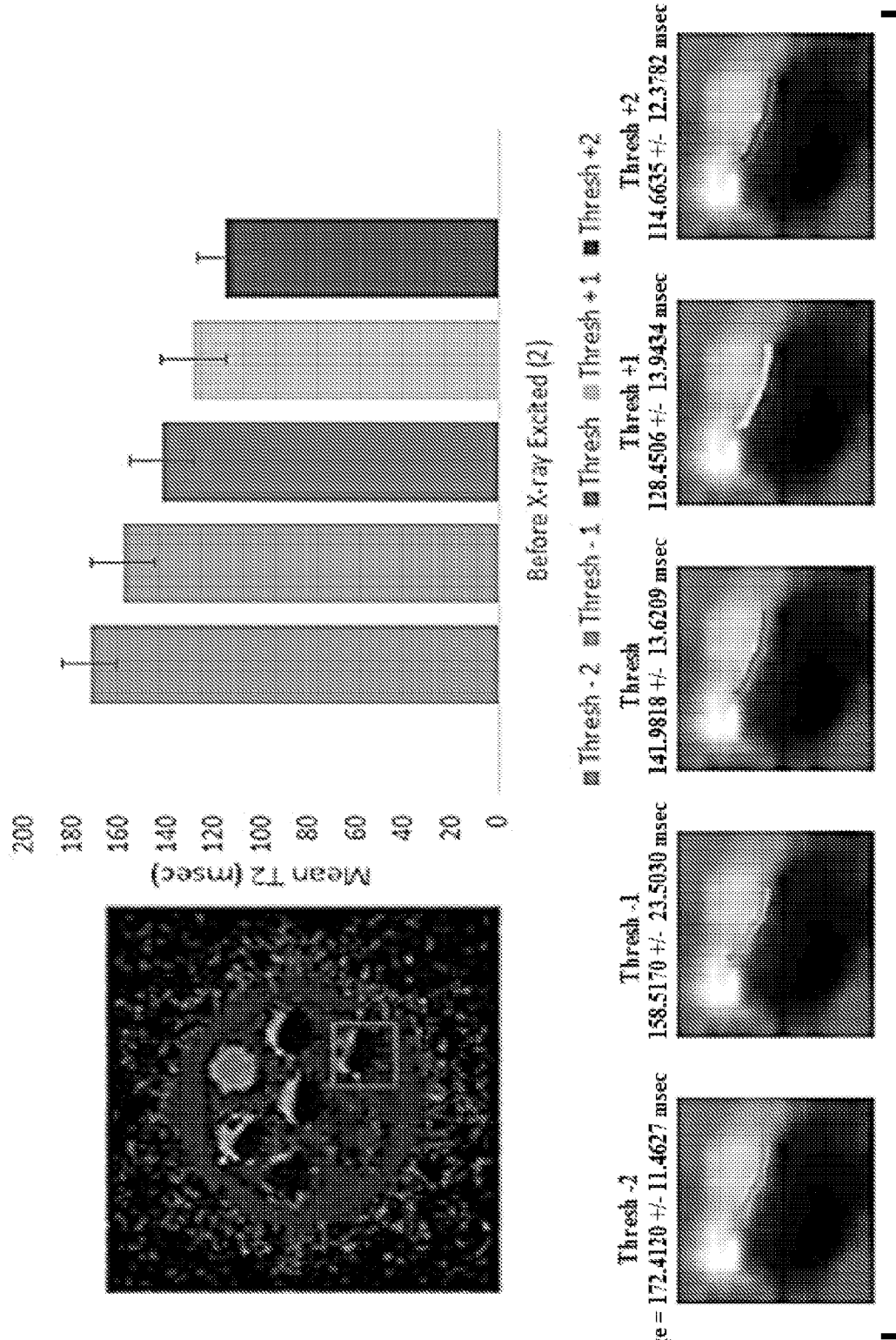
FIG. 37 shows an image of nanoparticles (top left), a bar graph showing mean $T_2$ relaxation time (top right), and images of samples.
Figure 38:
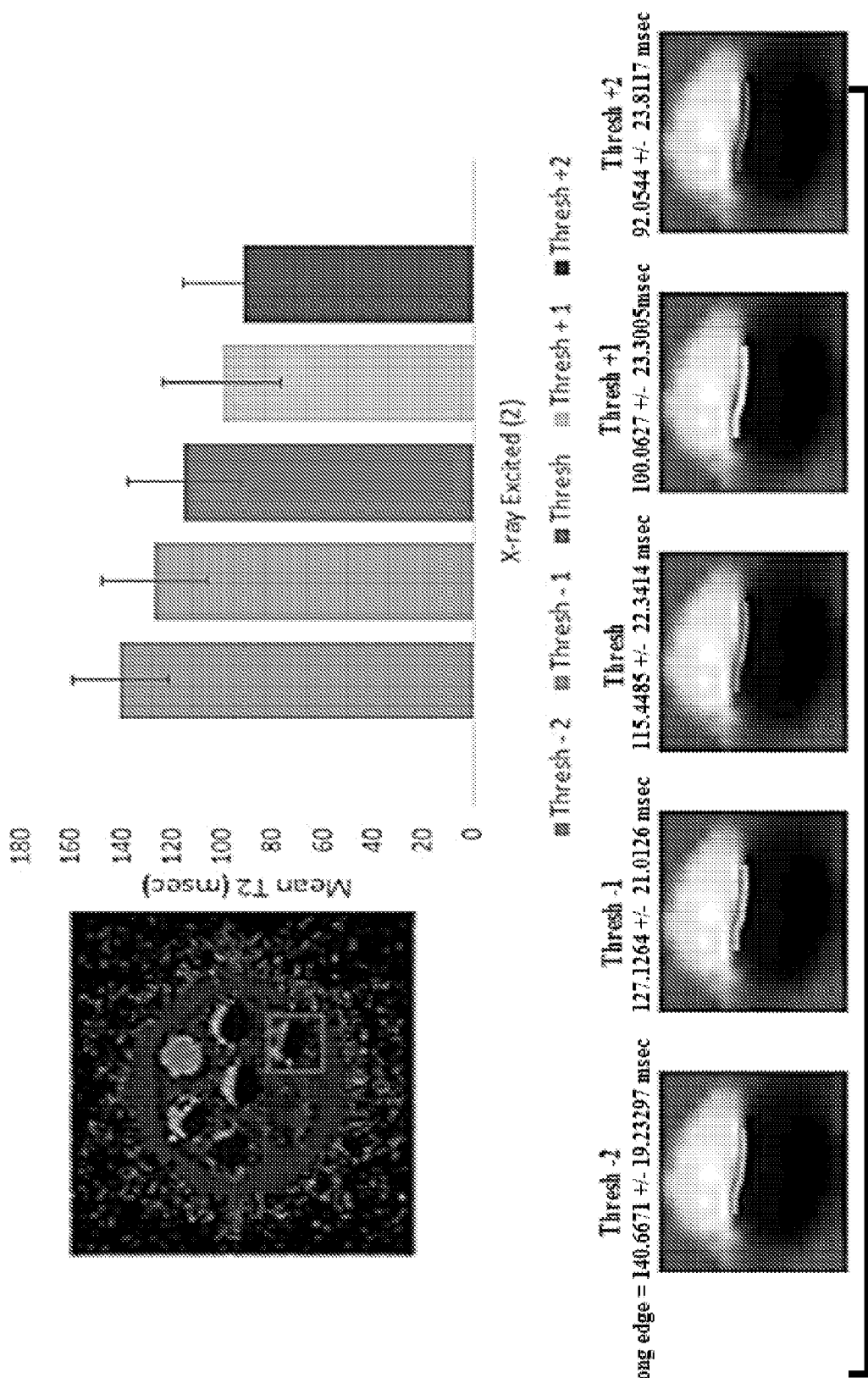
FIG. 38 shows an image of nanoparticles (top left), a bar graph showing mean $T_2$ relaxation time (top right), and images of samples.
Figures 39A, 39B, 39C, 39D:
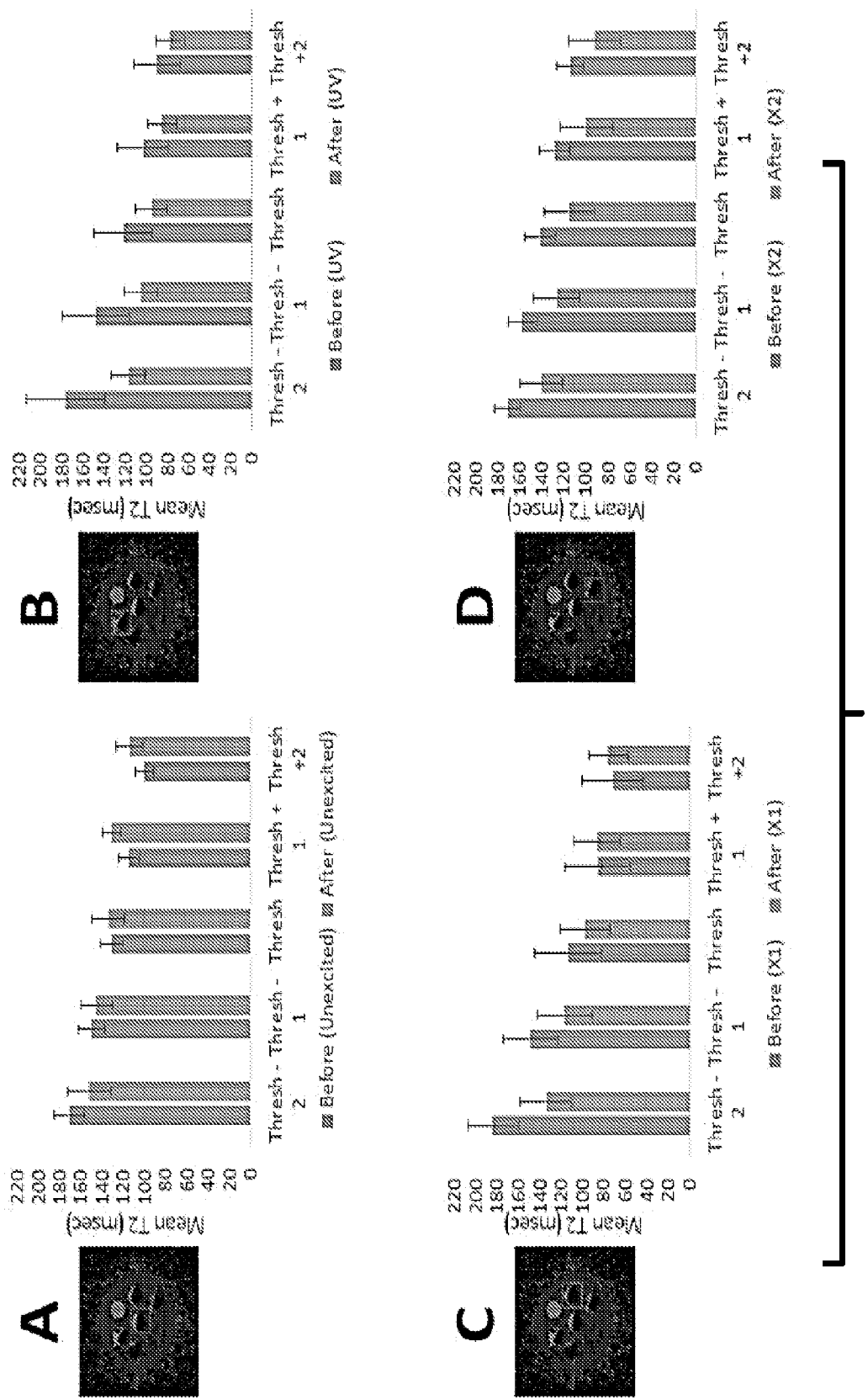
FIG. 39A shows an image of nanoparticles and a bar graph of an unexcited control.
FIG. 39B shows an image of nanoparticles and a bar graph of a UV-excited sample.
FIG. 39C shows an image of nanoparticles and a bar graph of an X-ray-excited sample.
FIG. 39D shows an image of nanoparticles and a bar graph of an X-ray-excited sample.

Further mean comparisons were made with adjusted threshold values. In this analysis, the edges were calculated after implementing adjusted threshold values and calculating the mean T2s along the new edges. FIG. 37 shows an image of nanoparticles (top left), a bar graph showing mean $T_2$ relaxation time (top right), and images of samples. FIG. 38 also shows an image of nanoparticles (top left), a bar graph showing mean $T_2$ relaxation time (top right), and images of samples. In each of FIGS. 37 and 38, the bars and the images from left to right are Thresh−2, Thresh−1, Thresh, Thresh+1, and Thresh+2. Referring to FIGS. 37 and 38 T2 increased when edges were taken more toward the water region (Thresh−value), and T2 decreased when edges were take more toward the NP region (Thresh+value).

Direct comparison for each of these edges was made to see if a change could be consistently detected between before- and after-excitation images as the edge was shifted into either of the regions. FIGS. 39A-39D show that in the excited samples (UV—FIG. 39B, X-ray1—FIG. 39C, X-ray2—FIG. 39D) the mean differences between the before- and after-excitation samples were increased as the edge moves further into the water regions. The unexcited control (FIG. 39A) also shows an increase in the mean difference between before- and after-excitation into the water region, but the trend for the unexcited control is not as consistent and distinct as for the excited counterparts.

The data advantageously show that the water coupled to nanophosphor slurries and excited by ionizing radiation such as UV or X-ray for 15 minutes is detected as having reduced $T_2$ relaxation time constants. Changes in relaxometry were most clearly observed along the edge of the slurry-water interface with changes extending somewhat into the bulk water phase. This is consistent with the physical understanding of the redistribution of electrons within semiconductor nanophosphors and the subsequent effects on nuclear relaxation. The acquisition and analysis of the data may be considered complicated by the non-colloidal behavior of the nanoparticles employed. The nanophosphors used in this example can remain in a stable X-ray excited state over long periods of time, thereby allowing for the particles to be excited outside of the MRI machine and remain excited during the high-resolution imaging sessions. Despite this vital advantage, these nanophosphors may behave poorly in aqueous environments. Within minutes of dispersing the particles in the water, more than 90% of the particles had settled to the bottom of the capillary tubes. After allowing the particles to settle for about an hour, water being excluded from the particle slurry was seen by a loss of MRI readable signal as a function of time.

The non-colloidal behavior can potentially lead to issues with sample control, stability, or homogeneity. While a robust characterization of a colloidal suspension may have some advantages, qualitative changes in water relaxation about the nanoparticle slurry-bulk water interface were detected once the samples were allowed to settle for 5-10 min before undergoing MRI scans. Variations in the water-slurry interfaces among the samples and scans of the same sample pre- and post-X-ray treatment can result in measurement variations. Further measurement error, possibly resulting in lower measured changes or larger standard deviations, may have also resulted from variable NP concentrations in the water regions of each sample. Regardless of the source of the variation, overlapping standard deviation ranges between samples before- and after-excitation can indicate a decrease in statistical significance.

Any experimental complications caused by non-colloidal nanophosphors can be mitigated through the use of nanophosphors (e.g., semiconducting nanophosphors) that can be more easily suspended or remain colloidal in aqueous solutions. Techniques that can be used according to embodiments of the subject invention for improving the water compatibility include milling or crystal growth to smaller particle sizes, coating, or conjugating the nanophosphors to hydrophilic polymers. These techniques also open doors for specific targeting of these nanophosphors to cells and proteins. Such conjugation could potentially decrease the direct interaction of water with the nanophosphor's electron distribution, resulting in less change in T2 after UV or X-ray excitation. Enhanced experimental control and robust statistical analysis methods such as paired t-tests can be used to help quantitatively demonstrate the effect of UV or X-ray excitation of nanophosphors on the T2 relaxation of surrounding water protons in a biologically relevant model.

Additionally, uncertainties in the T2 constants for water were high due to highly-efficient but sub-optimal sampling of its intensity during the relaxation period. The max TE used was about 180 msec, and, therefore, trying to fit water T2 constants that are greater than 300 msec may have resulted in some minor errors that could be improved with a different imaging protocol. If two primary T2s are present, a second T2 experiment with better TE sampling can be used for better T2 fits with less variation from voxel to voxel in both types of ROIs.

Because of the low resolution of the images at the sample level, each image underwent bicubic interpolation. Such methods are accepted for approximating data among measured points, though the various thresholds and subsequent edges calculated may have approximation errors during the T2 averaging. Also, to make sure if the change in T2s shown in the data is a result of the nanophosphor excitation, a repeated measurement with the same samples after discharging the nanophosphors can be performed. The persistence shown by these particles makes true discharge of the nanophosphors challenging.

As shown in this example, X-rays can be used to alter measured MRI signals through the use of nanophosphors (e.g., semiconducting nanophosphors). The link between X-rays, nanophosphors, and MRI can be utilized to advance imaging technology and deepen the understanding of multiphysics coupling.

Example 5

Figure 40:
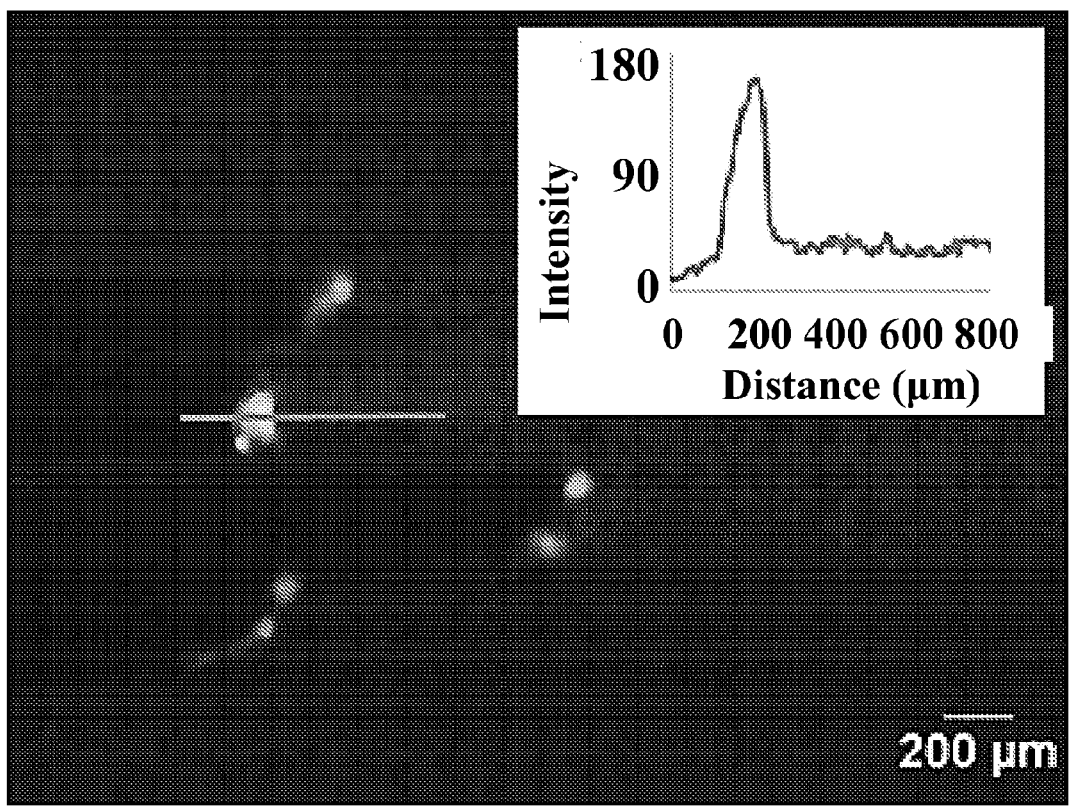
FIG. 40 shows an image resulting from subtracting an image without UV from an image with UV.

About 250 µL of nanophosphor ($Gd_2O_2S:Tb^{3+}$) suspensions of varying concentrations (0.1, 0.2, 0.4, and 0.8 mg/mL) in 0.5% agar were pipetted into a pair of glass slides separated by 0.75 mm plastic spacers and allowed to gel. This was done to verify that the UV LED source used for the remainder of this example was capable of causing the nanophosphors to emit phosphorescence. A Nikon TE2000 wide-field microscope (inverted epi-fluorescence mode; 10× objective lens) with an emission filter (bandwidth 40 nm at 535 nm, Chroma) was used to capture phosphorescence images both with and without UV excitation. Microscopy was performed in a dark environment, and the UV LED fibers were placed directly in the gels. Phosphorescence was qualitatively measured by subtracting the UV-off image from the UV-on image. FIG. 40 shows a result image from subtracting an image of 0.1 mg/mL $Gd_2O_2S:Tb^{3+}$ in 0.5% agar without UV from an image with UV. UV caused an increase in phosphorescence signal at the end of the fiber optic cables (plot profile inlaid). The full width at half maximum (FWHM) of the phosphorescence was 104 µm, indicating that any changes in MRI parameters should occur within about 100 µm of the fiber optic end.

Figure 12:
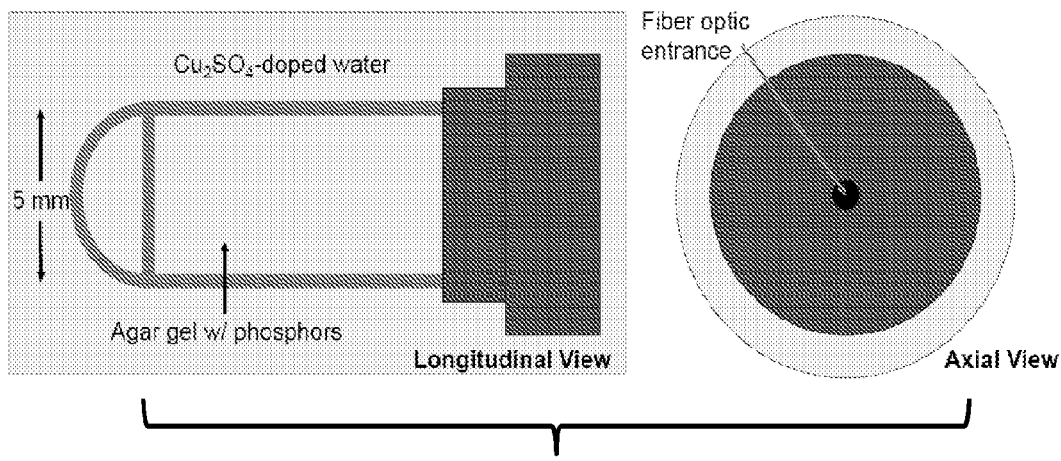
FIG. 12 shows a schematic view of a tube having nanoparticles.

The same stock suspensions used for the phosphorescence verification were then pipetted into 5 mm NMR tubes, capped, and placed within larger cuvettes filled with $Cu_2SO_4$-doped water. The fiber optical leads were thread through small holes in the caps of both the cuvette and nuclear magnetic resonance (NMR) tubes and centered by the placement of a small piece of foam in the top of the NMR tubes. FIG. 12 shows a schematic side view (left) and a schematic axial view (right) of a tube. The leads were placed directly into the agar gel and held in place by tape and parafilm.

Each sample was placed in a 23-mm RF coil and centered in a Bruker 13 cm, 7T horizontal bore MRI scanner. T1, T2, and T2* were quantitatively measured and mapped within the samples using the same protocols described in Example 4.

T2 was measured with a train of 16 TEs of equally spaced echoes of 10.5 ms and a TR of 1042.8 ms. Anisotropic voxels were taken to reduce the scan time with 256 px in the read-out direction and 128 px in the P1 direction. Because the field of view was 1.8 mm by 1.4 mm, the read-out resolution was 70 µm/px and the P1 resolution was 109 µm/px. Also, the slice thickness used was 1.2 5 mm. This geometry reduced the scan time to 2 min and 13 seconds. These scans were repeated with UV irradiation to test the effects of nanophosphor excitation and phosphorescence on the MRI parameters.

FIG. 40 shows the verification of emission phosphorescence under UV irradiation. Only the 0.1 mg/mL concentration suspension is shown, but all of the suspensions showed similar phosphorescence signatures. UV light is quickly attenuated in the agar samples, which is shown by the relatively shallow phosphorescence. This result indicates where MRI parameter changes are most likely to occur: within a few hundred microns of the fiber optic end.

Figure 41:
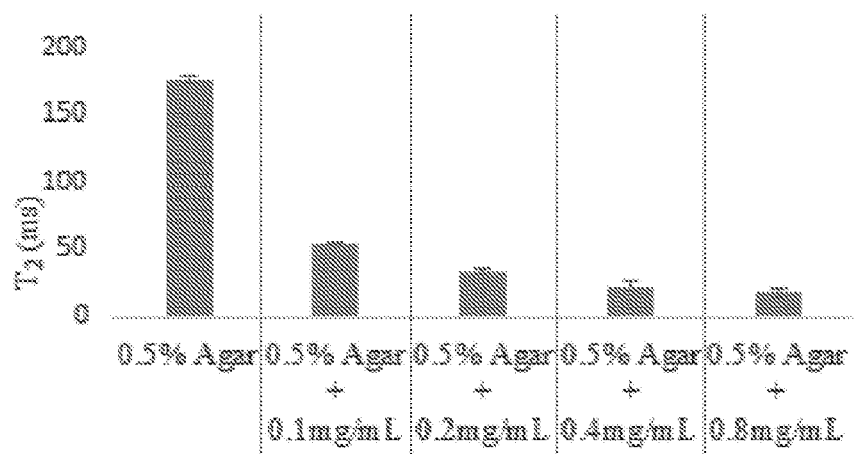
FIG. 41 shows a plot of T2 relaxation times.

FIG. 41 shows the intrinsic concentration-dependent contrast modulation by the $Gd_2O_2S:Tb^{3\pm}$. Referring to FIG. 41, T2 measurements decreased as the $Gd_2O_2S:Tb^{3+}$ concentration increased. Though not shown in FIG. 41, T1 and T2* also decreased as nanophosphor concentration increased. The results may have been limited due to slice thickness being about 6-fold wider than the fiber optic width. Results may have also been limited by the combination of shallow UV penetration through agar as well as the resolution of the MRI. Smaller slice thickness would likely give even more improved results. Also, the MRI parameters can be measured before, during, and after UV-irradiation. In addition, higher power UV and/or higher efficiency nanophosphors can be used to give even more improved results.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Carpenter C M, Sun C, Pratx G, Liu H, Cheng Z, et al. (2012) Radioluminescent nanophosphors enable multiplexed small-animal imaging. Opt Express 20: 11598-11604 (http://www.pubmedcentral.nih.gov/articlerender.fcgi?artid=3482915&tool=pmcentrez&rendertype=abstract).

Qin J, Peng C, Zhao B, Ye K, Yuan F, et al. (2014) Noninvasive detection of macrophages in atherosclerotic lesions by computed tomography enhanced with PEGylated gold nanoparticles. Int J Nanomedicine 9: 5575.

Naha P C, Al Zaki A, Hecht E, Chorny M, Chhour P, et al. (2014) Dextran coated bismuth-iron oxide nanohybrid contrast agents for computed tomography and magnetic resonance imaging. J Mater Chem B 2: 8239-8248.

Cong W, Wang C, Wang G (2014) Stored Luminescence Computed Tomography. Appl Opt 53: 5672-5676 (http://arxiv.org/abs/1309.3585).

Cong W, Liu F, Wang C, Wang G (2014) X-ray micro-modulated luminescence tomography (XMLT). Opt Express 22: 5572-5580.

Chuang Y-J, Zhen Z, Zhang F, Liu F, Mishra J P, et al. (2014) Photostimulable Near-Infrared Persistent Luminescent Nanoprobes for Ultrasensitive and Longitudinal Deep-Tissue Bio-Imaging. Theranostics 4: 1112.

Laurent S, Vander Elst L, Muller R N (2009) Lanthanide complexes for magnetic resonance and optical molecular imaging. Q J Nucl Med Mol imaging Off Publ Ital Assoc Nucl Med (AIMN)[and] Int Assoc Radiopharmacol (IAR),[and] Sect Soc of. 53: 586-603.

Elster A D (2014) Advanced Relaxation Theory. ELSTER LLC (http://www.mri-q.com/solomon-bloembergen.html).

F. Liu, W. Yan, Y.-J. Chuang, Z. Zhen, J. Xie, and Z. Pan, "Photostimulated near-infrared persistent luminescence as a new optical read-out from Cr3+-doped $LiGa_5O_8$.," *Sci. Rep.*, vol. 3, p. 1554, January 2013.

T. Maldiney, A. Lecointre, B. Viana, A. Bessière, M. Bessodes, D. Gourier, C. Richard, and D. Scherman, "Controlling electron trap depth to enhance optical properties of persistent luminescence nanoparticles for in vivo imaging.," *J. Am. Chem. Soc.*, vol. 133, no. 30, pp. 11810-5, August 2011.

S. Laurent, L. Vander Elst, and R. N. Muller, "Lanthanide complexes for magnetic resonance and optical molecular imaging.," *Q. J. Nucl. Med. Mol. imaging Off Publ. Ital. Assoc. Nucl. Med.* (*AIMN*) [and] *Int. Assoc. Radiopharmacol.* (*IAR*), [and] *Sect. Soc. of.*, vol. 53, no. 6, pp. 586-603, 2009.

H. Chen, T. Moore, B. Qi, D. C. Colvin, E. K. Jelen, D. A. Hitchcock, J. He, O. T. Mefford, J. C. Gore, and F. Alexis, "Monitoring pH-triggered drug release from radioluminescent nanocapsules with X-ray excited optical luminescence," *ACS Nano*, vol. 7, no. 2, pp. 1178-1187, 2013.

M. Getzin, Y. Xu, A. Rao, S. Madi, A. Bahadur, M. R. Lennartz, and G. Wang, "Carotid plaque characterization using CT and MRI scans for synergistic image analysis," in *SPIE Optical Engineering+Applications*, 2014, p. 92121B-92121B.

M. Getzin, L. Gjesteby, Y.-J. Chuang, S. McCallum, W. Cong, C. Wang, Z. Pan, G. Dai, and G. Wang, "A Pilot Study on Coupling CT and MRI through Use of Semiconductor Nanoparticles,"*arXiv Prepr. arXiv*1412.7554, 2014.

What is claimed is:

1. An imaging method, comprising:
providing a multi-physics coupling imaging device comprising:
a magnetic resonance imaging (MRI) system, a computed tomography (CT) system having a first X-ray source, and an X-ray focusing system having a second X-ray source and an X-ray focusing mechanism configured to shrink X-ray radiation beams emitted by the second X-ray source;
providing nanoparticles within a sample to be imaged;
positioning the sample within the multi-physics coupling imaging device;
exciting the nanoparticles within the sample by focused X-ray radiation emitted by the second X-ray source and focused by the X-ray focusing mechanism, the exciting is configured to result in a change of the energy state of the nanoparticles;
imaging the sample using the MRI system to obtain localization information of the nanoparticles by measuring a change in a resonance parameter of the nanoparticles as a result of the change in the energy state of the nanoparticles; and
imaging the sample using the CT system to obtain CT data from the sample simultaneously while imaging the sample using the MRI system.

2. The imaging method according to claim 1, wherein the nanoparticles are nanophosphors, and
wherein the nanophosphors are semiconducting crystals doped with lanthanide ions.

3. The imaging method according to claim 1, wherein the resonance parameter of the nanoparticles is T2 relaxation time.

4. The imaging method according to claim 1, wherein the sample is living tissue such that the method is performed in vivo.

5. The imaging method according to claim 4, wherein the living tissue is a brain or part of a brain of a human patient.

6. The imaging method according to claim 1, wherein the nanoparticles include $LiGa_5O_8:Cr^{3+}$, $MgGa_2O_4:Cr^{3+}$, $Gd_2O_2S:Tb^{3+}$, $CaMgSi_2O_6:Eu^{2+}$, $CaMgSi_2O_6:Mn^{2+}$, $CaMgSi_2O_6:Pr^{3+}$, or a combination thereof.

7. The imaging method according to claim 1, wherein the resonance parameter is T1, T2, or T2*.

8. The imaging method according to claim 1, wherein imaging the sample using the MRI system to obtain localization information of the nanoparticles by measuring a change in a resonance parameter of the nanoparticles as a result of the change in the energy state of the nanoparticles comprises measuring the resonance parameter of the nanoparticles before and after excitation by the second X-ray source.

9. An imaging system, comprising:
a multi-physics coupling imaging device comprising:
- a magnetic resonance imaging (MRI) system, a computed tomography (CT) system having a first X-ray source, and an X-ray focusing system having a second X-ray source and an X-ray focusing mechanism configured to shrink X-ray radiation beams emitted by the second X-ray source;
- wherein the second X-ray source is configured to supply X-ray radiation focused by the X-ray focusing mechanism to nanoparticles provided within a sample to be imaged, wherein the radiation is configured to excite the nanoparticles into an excited energy state;
- wherein the MRI system is configured to obtain MRI data of the sample before and after the excitation by the second X-ray source;
- wherein the CT system is configured to obtain CT data of the sample simultaneously with the MRI system obtaining the MRI data; and
a processor configured to determine localization information of the nanoparticles provided within the sample by measuring a change in a resonance parameter of the nanoparticles as a result of the change in the energy state of the nanoparticles.

10. The imaging system according to claim 9, wherein the nanoparticles are nanophosphors, and
wherein the nanophosphors are semiconducting crystals doped with lanthanide ions.

11. The imaging system according to claim 9, wherein the resonance parameter of the nanoparticles is T2 relaxation time.

12. The imaging system according to claim 9, wherein the sample is living tissue such that the system is capable of performing in vivo imaging.

13. The imaging system according to claim 12, wherein the living tissue is a brain or part of a brain of a human patient.

14. The imaging system according to claim 9, wherein the nanoparticles include $LiGa_5O_8:Cr^{3+}$, $MgGa_2O_4:Cr^{3+}$, $Gd_2O_2S:Tb^{3+}$, $CaMgSi_2O_6:Eu^{2+}$, $CaMgSi_2O_6:Mn^{2+}$, $CaMgSi_2O_6:Pr^{3+}$, or a combination thereof.

15. The imaging system according to claim 9, wherein the resonance parameter is T1, T2, or T2*.

* * * * *